US008618082B2

(12) United States Patent
Mukhtar et al.

(10) Patent No.: US 8,618,082 B2
(45) Date of Patent: Dec. 31, 2013

(54) LUPEOL ANTI-TUMOR AGENT AND USES THEREOF

(75) Inventors: Hasan Mukhtar, Fitchburg, WI (US); Mohammad Saleem Bhat, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1137 days.

(21) Appl. No.: 10/906,691

(22) Filed: Mar. 2, 2005

(65) Prior Publication Data

US 2005/0201956 A1 Sep. 15, 2005
US 2006/0062745 A2 Mar. 23, 2006

Related U.S. Application Data

(60) Provisional application No. 60/549,386, filed on Mar. 2, 2004.

(51) Int. Cl.
*A01N 45/00* (2006.01)
*A61K 31/56* (2006.01)

(52) U.S. Cl.
USPC .......................................... 514/169

(58) Field of Classification Search
USPC .................................... 424/59; 514/169, 557
See application file for complete search history.

(56) References Cited

U.S. PATENT DOCUMENTS 5,962,527 A * 10/1999 Pezzuto et al. ................ 514/569
6,110,907 A * 8/2000 Au-Yeung et al. ............ 514/185
6,200,573 B1 * 3/2001 Locke ........................... 424/727
6,413,953 B1 * 7/2002 Gianomenico et al. ....... 514/188

FOREIGN PATENT DOCUMENTS

WO  2006031756 A2  3/2006

OTHER PUBLICATIONS

K. Yasukawa et al. Phytomedicine, 1995, 4, 309-313.*
Sarwat Sultana et al. Indian Journal of experimental Biology, 2003, 41, 827-831.*
Keishi Hata et al. Biol. Pharm. Bull., 2000, 23, 962-967.*
Medline Plusâ: Medical Encyclopedia: Skin cancer retrieved online on May 30, 2007 from the internet https://www.nlm.nih.gov/medlineplus/print/ency/article/001442.htm, p. 1-3 dated on Oct. 26, 2006.*
Medline Plusâ: Medical Encyclopedia: Prostate cancer retrieved online on May 30, 2007 from the internet https://www.nlm.nih.gov/medlineplus/print/ency/article/000380.htm, p. 1-5 dated on Sep. 11, 2006.*
Medline Plusâ: Medical Encyclopedia: Pancreatic carcinoma retrieved online on May 30, 2007 from the internet https://www.nlm.nih.gov/medlineplus/print/ency/article/000236.htm, p. 1-3 dated on Sep. 11, 2006.*
Zips et al. In vivo 2005, 19:1-8.*
Definition: parenteral from online Medical Dictionary date on Nov. 18, 1997.*
Iguchi et al. (The Prostse, 2001, 47:59-65).*
Abuchowski, et al. (1981).
Afaq, F, et al. (2003). Oncogene., 22, 1035-1044.
Ahmad, N., et al. (2001). Am. J. Pathol., 159, 885-892.
Ahmad, N., et al. (2000). Clin. Cancer Res., 6, 1524-1528.
Anjaneyulu, V., et al. (1982). Indian J.Pharm. Sci., 44, 58-59.
Auvinen, M. (1997). J. Natl. Cancer Inst., 89, 533-537.
Baeuerle, P.A. and Baltimore, D. (1996). Cell., 87, 13-20.
Baldwin, Jr., A.S., (1996). Annu. Rev. Immunol., 14, 649-683.
Beveridge, T.H., et al., (2002). J. Agric. Food Chem., 50, 744-760.
Bhimani, R.S., at al., (1993). Inhibition of oxidative stress in HeLa cells by chemopreventive agents. Cancer Res., 53, 4528-4533.
Bickers, D.R. and Athar, M. (2000). J. Dermatol., 27, 691-695.
Bours, V., et al, (2000). Biochem. Pharmacol., 80, 1085-1089.
Buchwald, et al., (1980) Surgery 88:507.
Callejas, N.A., et al., (1999). J. Cell. Sci., 18, 3147-3155.
Carpenter, C.L. and Cantley, L.C. (1996). Curr. Opin. Cell. Biol., 8, 153-158.
Chun, K.S., et al., (2002). J. Environ. Pathol. Toxicol, Oncol., 21, 131-139.
Conney, et al., (1997) Proc. Soc. Exp. Biol. Med., 216, 234-245.
Digiovanni, J. (1992). Pharmacol. Ther., 54, 63-128.
Digiovanni, J. (1991). Modification of Tumor Development in Rodents : Progress in Experimental Tumor Research. Ito N and Sugano H (ed). Karger : Basel, 33, pp. 192-229.
Dos Santos, P.A. and De Aquino Neto, F.R., (2003). Z. Naturforsch [C], 58, 201-206.
Downward, J., (1998). Curr. Opin. Cell Biol., 10, 262-267.
Einspahr, J.G., et al., (2003). Recent Results Cancer Res, 163, 151-164.
Epinat, J.C. and Gilmore, T.D., (1999). Oncogene., 18, 6896-6909.
Fernandez, M.A., et al., (2001). J. Pharm. Pharmacol., 53, 1533-1539.
Fournet, et al., (1992). J. Ethnopharmacol., 37, 159-164.
Furstenberger, G. and Marks, F., (1985). Arachidonic Acid Metabolism and Tumor Promotion, 49-72.
Geetha, T. and Varalakshmi, P., (1999). Mol. Cell Biochem., 201, 83-87.
Geetha, T. and Varalakshmi, P., (2001). J. Ethnopharmacol., 76, 77-80:.
Goodson, (1984). Medical Applications of Controlled Release, supra, vol. 2, 115-138.
Guevara, A.P., et al., (1996). Mutat. Res., 361, 67-72.
Gupta, S. and Mukhtar, H., (2001). Skin Pharmacol. Appl. Skin Physiol.; 14, 373-385.
Gupta, S. and Mukhtar, H., (2002). Cancer Metastasis Rev., 21, 363-380.
Gupta, S., et al., (1999). Cancer Res., 59, 2115-2120.
Hasmeda, M., et al., (1999). Planta Med., 65, 14-18.
Hata, K., et al., (2002). J. Nat. Prod., 66, 645-648,.

(Continued)

*Primary Examiner* — Mina Haghighatian
*Assistant Examiner* — Helen Chui
(74) *Attorney, Agent, or Firm* — Quarles & Brady LLP

(57) ABSTRACT

The present invention provides methods for the prevention, treatment and/or alleviation of skin disorders and skin cancers and prevention, treatment and/or alleviation of prostate cancer and pancreatic cancer by administering a Lupeol-derived anti-tumor compound. The invention further provides pharmaceutical and nutraceutical compositions containing Lupeol-derived anti-tumor compounds.

5 Claims, 15 Drawing Sheets

(56) References Cited

OTHER PUBLICATIONS

Hata, K., et al., (2003). J. Biochem (Tokyo), 134, 441-445.
Herschman, H.R., (1994). Cancer Metastasis Rev., 13, 241-256.
Hodges, L.D., et al., (2003). Mol. Cell. Biochem., 252, 97-101.
Israel, A., (1995). Trends Genet., 11, 203-205.
Kakuda, R., et al., (2002). Phytochemistry., 59, 791-794.
Katiyar, S.K., et al., (1999). Carcinogenesis., 20, 2117-2124.
Katiyar, S.K. and Mukhtar H. (1997). Carcinogenesis., 18, 1911-1916.
Katiyar, S.K., et al., (1996). Cancer Res., 56, 1023-1030.
Katiyar, S.K., et al., (1997). Carcinogenesis., 18, 497-502.
Katre, et al., (1987).
Kim, D.J., et al., (2003). Mutat Res., 523-524, 99-107.
Langer, (1990). Science 249:1527-1533.
Liang, Y.C., et al., (2002). Nutr. Cancer., 42, 217-223.
Lin, L.C., et al., (2001). J. Nat. Prod., 64, 674-676.
Luo, J., et al., (2003). Cancer Cell., 4, 257-262.
Maniatis, T., (1997). Science., 278, 818-819.
Mills, G.B., et al., (2003). Semin. Oncol., 30, 93-104.
Miura, K., et al., (2001). Phytochemistry., 58, 1171-1175.
Mohan, R.R., et al., (1999). Clin. Cancer Res., 5, 143-147.
Moriarity, D.M., et al., (1998). Planta Med., 64, 370-372.
Nagaraj, M., et al., (2000). J. Appl. Toxicol., 20, 413-417.
Nakadate, T., et al., (1985). Jpn. J. Pharmacol., 37, 253-258.
Sefton, M.V. Crit. Rev. Bio. Eng. 14, 201-40 Year, : 1987.
Nikiema, J.B., et al., (2001). Phytother. Res., 15. 131-134.
Osaki, M., el al., (2004) J. Cancer Res. Clin. Oncol., 130, 8-14.
Rajic, A., et al., (2000). Planta Med., 66, 206-210.
Romashkova, J.R. and Makarov, S.S., (1999). Nature, 401, 86-90.
Saeed, M.A., and Sabir, A.W., (2002). Fitoterapla, 73, 417-420.
Saleem, M., et al., (2001). Pharmacol. Res., 43, 127-134.
Saleem, R., et al., (2003). Biol. Pharm, Bull., 26, 41-46.
Saudek, et al., (1989). N. Engl. J. Med. 321:574.
Seo, et al., (2002). Int. J. Cancer, 100, 456-462.
Smith, W.L., et al., (1996). J. Biol. Chem., 271, 33157-33160.
Sosa, A., (1963). Bull. Soc. Chim. Bio. (Paris)., 45, 117-128.
Stambolic, V., et al., (1999). Oncogene., 18, 6094-6103.
Sunitha, S., et al., (2001). Fitoterapia, 72, 516-523.
Surth, Y.J., (2003). Nat. Rev. Cancer., 3, 788-780.
Thomas, T., and Thomas, T.J., (2003). J. Cell. Mol. Med., 7, 113-126.
Treat, et al., (1989). Liposomes in the Therapy of Infectious Disease and Cancer, Lopez-Berestein and Fidler (eds), Liss, N.Y., 353-365.
Ulubelen, A., et al., (1997). J. Nat. Prod., 60, 1275-1280.
Verma, A.K., et al., (1979). Cancer Res., 39, 419-425.
Vidya, L., et al., (2002). Phytother, Res., 16, 514-518.
Wada, S., et al., (2001). J. Nat. Prod., 64, 1545-1547.
Ziegler, H.L., et al., (2002). Antimicrob. Agents Chemother., 46, 1441-1446.

* cited by examiner

LUPEOL [Lup-20(29)-en-3β-ol]

Caspase proteins induces apoptosis (programmed cell death) of cells. In prostate cancer cells these caspases are in inactive form. Lupeol treatment to LNCaP cells induces the activation of Caspase-8 and 9 proteins which ultimately provide signal to cancer cells to undergo apoptosis.

As in figure below, the treatment of Lupeol causes disappearance of inactive caspases which is a clear indication that caspases have been turned into active form which participate in the process of apoptosis.

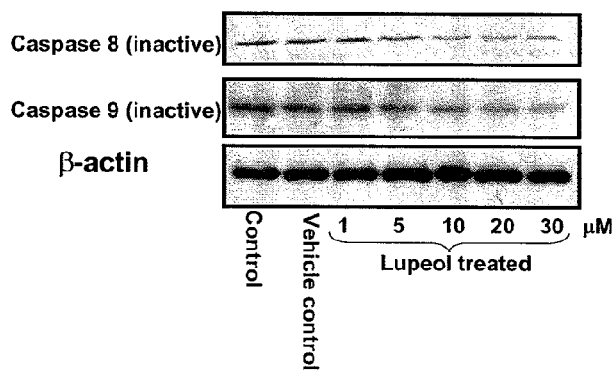

Figure 6

Fas (also known as CD-95) is a death receptor protein and FADD is an adaptor protein which receives the death signal from FAS and transmits it to other proteins participating in apoptosis mechanism. Fas has a death domain sequence. Lupeol treatment induces the expression of FAS receptor protein and FADD protein in prostate cancer cells. No other death receptor such as TNFR1, DR4/5 were activated by Lupeol (data not shown).

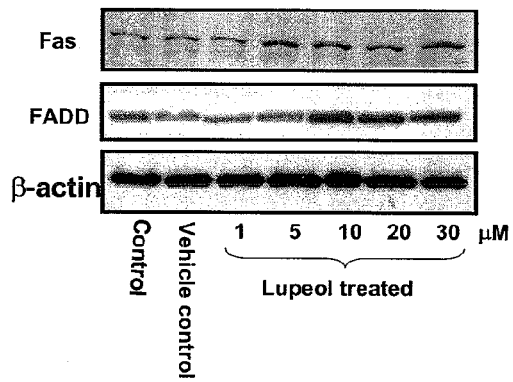

Figure 7

Anti-Fas antibody (anti-Fas mAb) activates the Fas protein. We observed that LNCaP cells when treated with anti-Fas antibody, it caused a 45% cell death in at a 1 µg at 48 hours of treatment.

However when anti-Fas mAb pretreated LNCaP cells were treated with Lupeol (30 µg), there was 95-98% cell death. This result suggest that Lupeol acted in a significant synergistic manner and caused more cell death than the cumulative effects of Lupeol alone or ant-Fas antibody alone.

mAb= monoclonal antibody

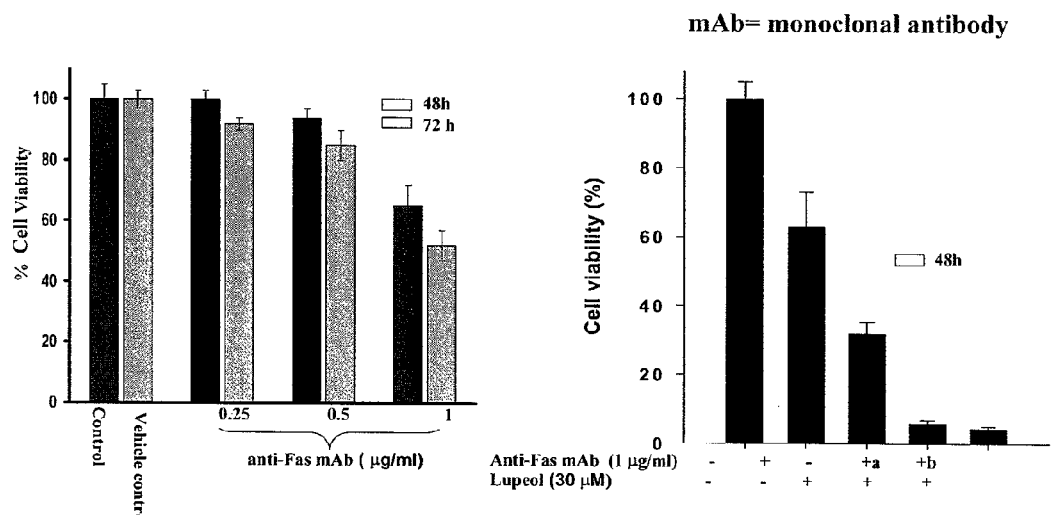

Figure 8

As seen in figure below, Fas protein expression was found to be highly increased in anti-Fas mAb pretreated LNCaP cells treated with Lupeol. This result suggest that Lupeol has A potential to induce the Fas protein expression that ultimately leads to apoptotic cell death of prostate cancer cells.

mAb= monoclonal antibody

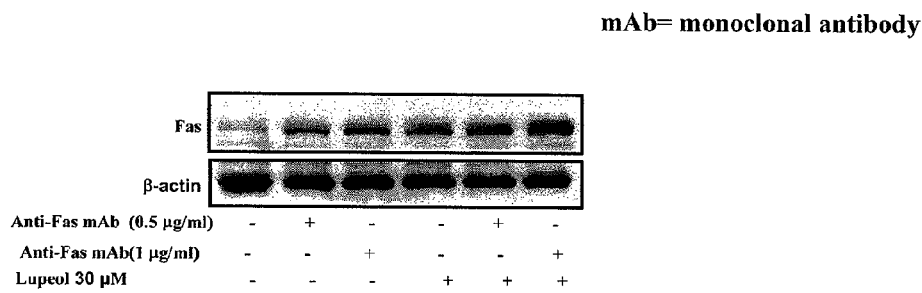

Figure 9

To determine whether Lupeol induces apoptosis of LNCaP cells selectively through Fas receptor, we used siRNA technology. siRNA's have the ability to silence the of any specific protein. We designed siRNA against Fas receptor protein and treated LNCaP cell with them. The Fas protein expression was significantly reduced in LNCaP cells treated siRNA which suggested that these cells had no or minimal Fas receptor expression. When Fas-silenced LNCaP cells were treated with Lupeol, there was reduced cell death as compared to LNCaP cells (which had Fas receptors expression) treated with Lupeol. This data clearly suggest that Lupeol induced death of LNCaP cells is through Fas receptor.

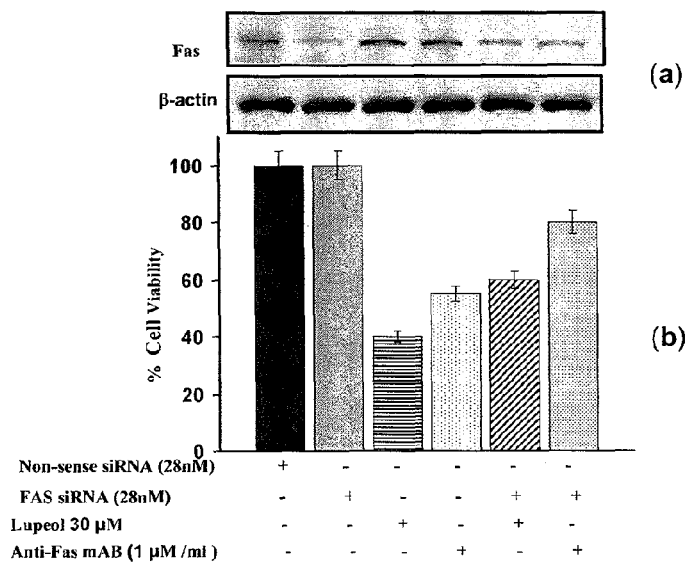

Figure 10

To determine, whether lupeol could reduce the tumorigenicity of prostate cancer cells in animal model, androgen-dependent prostate cancer cells CW22Rv1, were implanted in a Athymic nude mouse xenograft model. Mice were given i.p. injection of Lupeol (1 mg/animal) three times a week. Tumor growth was measured weekly in terms of volume of tumors as function of time. The tumor growth in Lupeol treated mice was significantly Lower than control mice.

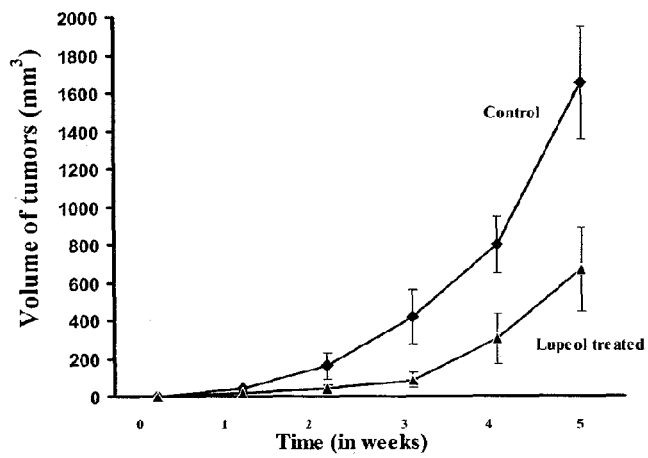

Figure 11

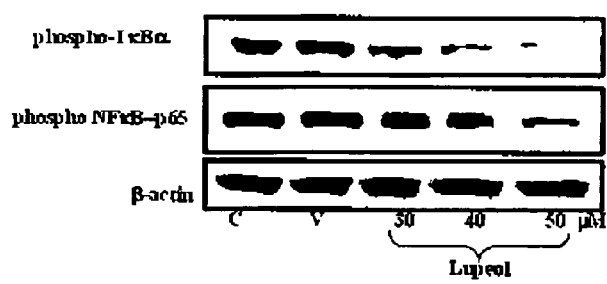
Figure 24
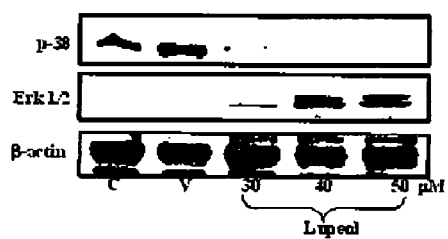 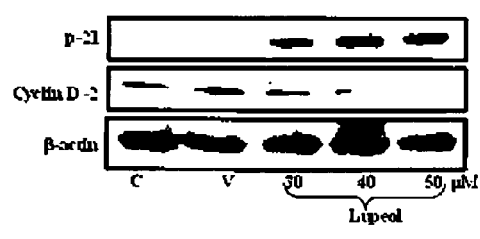
(a) (b)
Figure 25

LUPEOL ANTI-TUMOR AGENT AND USES THEREOF

RELATED APPLICATION

The present application seeks priority from U.S. Provisional Application 60/549,386, filed on Mar. 2, 2004, which is incorporated herein by reference for all purposes.

STATEMENT REGARDING FEDERALLY-SPONSORED RESEARCH

The present invention is supported in part by NIH grants CA78809 and CA99909. The government of the United States may have certain rights in this invention.

FIELD OF INVENTION

This invention relates to the inhibition, reduction and prevention of cancer. More particularly, the invention relates to compounds and methods for inhibiting skin cancer, prostate cancer and pancreatic cancer.

BACKGROUND OF THE INVENTION

Chemoprevention has become an effective cancer control modality, however, the search for novel agent(s) for the armamentarium of cancer chemoprevention continues. Therefore, agents capable for inhibition of promotion stage of tumorigenesis with the ability to intervene at several critical pathways in the tumorigenesis process have greater advantage over other single-target agents are highly desirable.

To reduce the occurrence of cancer, one promising approach is its prevention, specifically by chemical intervention through minor non-nutrient dietary constituents. Important to chemoprevention is the fact that carcinogenesis is a long term process of cellular growth, division and subsequent clonal expansion of initiated cells exemplified by steps known as initiation, promotion and progression (Gupta and Mukhtar, 2002). One advantage of chemoprevention is that agents can be targeted against each stage of tumorigenesis. Thus, inhibition or slowing of any stage of carcinogenesis can potentially prevent cancers from becoming clinically significant.

The intervention of cancer at the promotion stage, however, seems to be most appropriate and practical. The major reason for this is the fact that tumor promotion is a reversible event at least in early stages and requires repeated and prolonged exposure of a promoting agent (Bickers and Athar, 2000). For this reason, it is important to identify anti-tumor promoting agents. A number of compounds have been evaluated by the inventors' laboratory and others, for their potential chemopreventive activity, and many of them are of plant origin (Gupta and Mukhtar, 2001). Therefore, considerable attention has been focused on identifying edible and medicinal phytochemicals that possess the ability to interfere with carcinogenic or mutagenic processes (Conney et al., 1997; Surh, 2003).

Lupeol [Lup-20(29)-en-3β-ol] is a naturally occurring triterpene found in various fruits, vegetables and in many medicinal plants (FIG. 1). Of particular note is that a significant quantity of this compound is present in olive, mango, strawberry and fig plants (Sosa, 1963; Anjaneyulu et al., 1982; Saeed and Sabir, 2002). Lupeol is found as an active constituent of various medicinal plants used by native people in the treatment of various skin aliments in North America, Japan, China, Latin America and Caribbean islands (Fournet et al., 1992; Lin et al., 2001; Miura et al., 2001; Beveridge et al., 2002; Kakuda et al., 2002; Badria et al., 2003; Santos Pereira and De Aquino Neto, 2003). Lupeol also has been shown to possess various pharmacological properties (Ul-ubelen et al., 1997; Geetha and Varalakshmi, 1999; Nagaraj et al., 2000; Sunitha et al., 2001; Vidya et al., 2002; Saleem et al., 2003). Lupeol has been shown to possess strong anti-inflammatory, anti-arthritic, anti-mutagenic and anti-malarial activity in vitro and in vivo systems (Guevara et al., 1996; Geetha and Varalakshmi, 1999; Geetha and Varalakshmi, 2001; Ziegler et al., 2002). Lupeol has been shown to act as a potent inhibitor of protein kinases and serine proteases (Hasmeda et al., 1999; Rajic et al., 2000; Hodges et al., 2003) and inhibit the activity of DNA topoisomerase II, a target for anti-cancer chemotherapy (Moriarity et al., 1998; Wada et al., 2001). Lupeol has also been shown to improve the epidermal tissue reconstitution (Nikiema et al., 2001). Recent studies have shown that Lupeol induces differentiation and inhibits cell growth of melanoma cells (Hata et al., 2002; 2003).

SUMMARY OF THE INVENTION

The present invention provides numerous methods and pharmaceutical and nutraceutical compositions for treatment, inhibition, recurrence and occurrence of skin, prostate or pancreatic tumorigenesis, or cancer related conditions.

One preferred embodiment of the present invention provides a method for preventing skin, prostate or pancreatic tumorigenesis related conditions in a subject having those risks comprising the step of administering to the subject an effective amount of a compound having the formula:

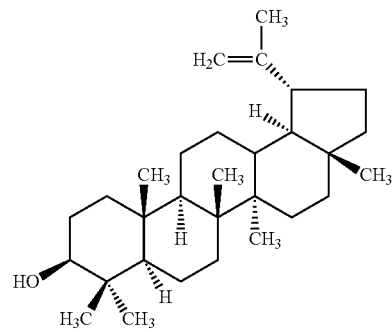

Tumorigenesis related conditions may include edema, hyperplasia, neoplasia, tumor or combinations thereof. The compound further inhibits tumorigenesis in a dose dependent manner. The compound may be administered topically or intraperitoneally to the subject. The compound may also be administered in a pharmaceutically acceptable carrier, including an emollient or a patch. The compound further inhibits induction of ODC activity, ODC protein, COX-2 protein expression, iNOS protein expression, expression of catalytic and regulatory subunits of PI3K, phosphorylation of Akt, phosphorylation of IκB protein, activation of IKKα, activation and nuclear translocation of NFκB/p65, or NFκB DNA binding.

Another preferred embodiment of the present invention provides a method of preventing the occurrence or recurrence of skin, prostate or pancreatic cancer in a subject in risk thereof. The method comprises the step of administering to said subject an effective amount of (a) an anti-tumor compound having the structure:

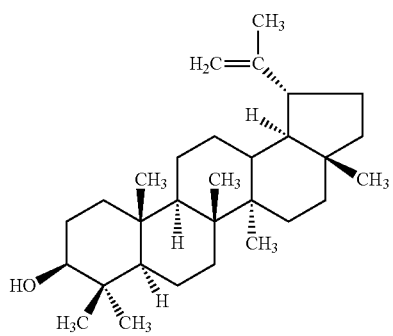

or (b) a pharmaceutically acceptable salt of said compound. The compound further inhibits skin, prostate or pancreatic cancer in a dose dependent manner and may be administered topically to the subject. The compound may also be is administered in a pharmaceutically acceptable carrier, including an emollient or a patch. Further the compound inhibits induction of ODC activity, ODC protein, COX-2 protein expression, iNOS protein expression, expression of catalytic and regulatory subunits of PBX, phosphorylation of Akt, phosphorylation of IκB protein, activation of IKKα, activation and nuclear translocation of NFκB/p65, or NFκB DNA binding. The occurrence or reoccurrence of skin, prostate or pancreatic cancer may include conditions such as edema, hyperplasia, tumor or neoplasia.

Yet another preferred embodiment of the present invention provides a pharmaceutical composition comprising (a) a compound having the formula:

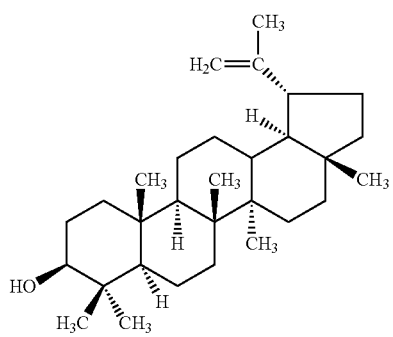

or (b) a pharmaceutically acceptable salt of said compound; and (c) a pharmaceutically-acceptable carrier. The compound may be available in a pharmaceutically acceptable carrier such as an emollient or a patch.

Yet another preferred embodiment of the present invention provides a method of providing nutraceutical benefits to a subject. The method comprises the step of administering to the subject a nutraceutical composition including (a) a compound having the formula:

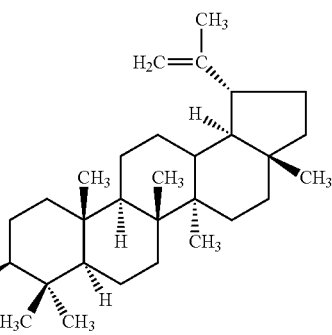

or (b) a pharmaceutically-acceptable salt of said compound; and (c) an acceptable carrier. The nutraceutical composition further comprises an immune boosting agent, anti-arthritic agent, anti-inflammatory agent, anti-oxidant anti-mutagenic agent, anti-malarial agent, or a mixture thereof.

Yet another preferred embodiment of the present invention includes a nutraceutical composition comprising: (a) a compound having the formula:

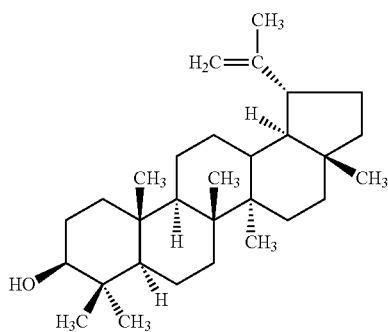

or (b) a pharmaceutically-acceptable salt of said compound; and (c) an acceptable carrier. The nutraceutical composition according further comprises an immune boosting agent, anti-arthritic agent, anti-inflammatory agent, anti-oxidant anti-mutagenic agent, anti-malarial agent, or a mixture thereof. Another preferred embodiment of the present invention provides a pharmaceutical composition comprising (a) a compound having the formula:

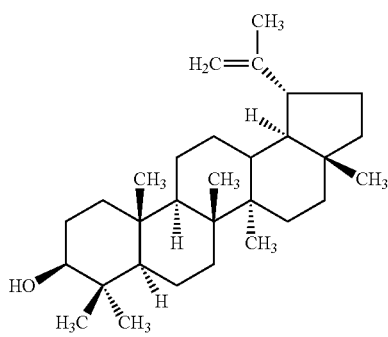

or (b) a pharmaceutically acceptable salt of said compound; and (c) a sunscreen lotion or cream.

Other objects, features and advantages of the present invention will become apparent from the specification, claims and drawings.

BRIEF DESCRIPTION OF DRAWINGS

FIG. 6. Inhibitory effect of Lupeol on TPA-induced activation of IKKα, and phosphorylation and degradation of IκBα in CD-1 mice: At different times after treatment, the animals were sacrificed, epidermal cytosolic was prepared, and protein expression was determined. Equal loading was confirmed by stripping the immunoblot and reprobing it for β-actin. The immunoblots shown here are representative of three independent experiments with similar results. The values above each lane indicate relative density of the band normalized to β-actin.

FIG. 7. Inhibitory effect of Lupeol on TPA-induced NF-κB activation and its subsequent translocation to nucleus in CD-1 mice. (a) At different times after treatment, the animals were sacrificed, nuclear lysates were prepared, and protein expression was determined. The values above each lane indicate relative density of the band.

Figure 1:
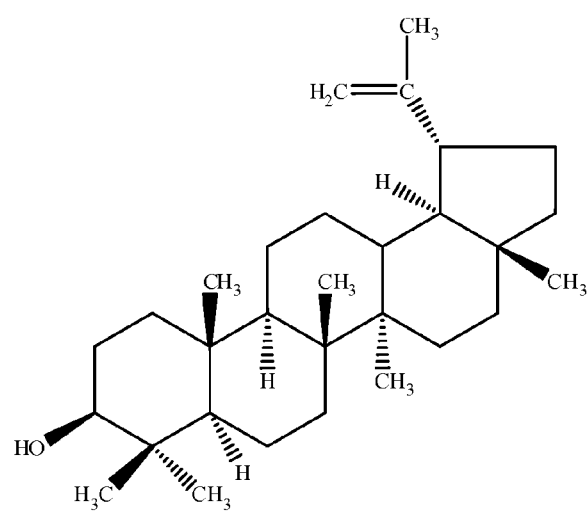
FIG. 1. Structure of Lupeol

(b) At different times after treatment, the animals were sacrificed, nuclear lysates were prepared, and DNA binding was determined by electron mobility shift assay as described under 'Materials and Methods'. C1, C2, and C3 refer to inter experimental controls, where C1 represents biotin-EBNA (epistein barr virus nuclear antigen) control DNA, C2 represents Biotin-EBNA control DNA and EBNA extract and C3 represents Biotin-EBNA control DNA and EBNA extract plus 200 fold molar excess of EBNA DNA. In C1 no protein extract for DNA to bind resulted in an unshifted band. In C2 sufficient target protein resulted in DNA-protein binding resulting in shift detected by comparison to band at position C1. C3 demonstrated that the signal shift observed in C2 could be prevented by competition from excess unlabelled DNA.

FIG. 8. Two stage carcinogenesis tumor data in CD-1 mice: Inhibitory effect of Lupeol on DMBA-initiated and TPA-promoted tumor formation in CD-1 mice: In each group, 20 animals were used. Tumorigenesis was initiated in the animals by a single topical application of 200 nmol DMBA in 0.2 ml vehicle on the dorsal shaved skin, and 1 week later, the tumor growth was promoted with twice-weekly applications of 3.2 nmol TPA in 0.2 ml vehicle. To assess its anti-skin tumor-promoting effect, Lupeol at a dose of 2 mg/animal was applied topically 30 min prior to each TPA application in different groups. Treatment with TPA alone or Lupeol plus TPA was repeated twice weekly up to the termination of the experiments at 28 weeks. Animals in all the groups were watched for any apparent signs of toxicity, such as weight loss or mortality during the entire period of study. Skin tumor formation was recorded weekly, and tumors larger than 1 mm in diameter were included in the cumulative number only if they persisted for 2 weeks or more. The tumor data is represented as the percentage of mice with tumors (a), the number of tumors per mouse (b) and the number of tumors per group (c). The data was analyzed by Wilcoxon rank sum test and $\chi^2$ analysis.

FIG. 9 depicts effect of Lupeol on viability of normal human prostate epithelial cells (PrEC). Cells were treated with specified concentrations of Lupeol for 48 h, and cell viability was determined by MTT (3-[4,5-dimethylthiazol-2-yl]-2,5-diphenyl tetrazoliumbromide) assay. The values are represented as the percent viable cells where vehicle-treated cells were regarded as 100% viable. Data represents mean value of percent viable cells±S.E of three independent experiments.

FIG. 10 depicts effect of Lupeol on viability of androgen-sensitive prostatic cancer cells (LNCaP). Cells were treated with specified concentrations of Lupeol for 48 h, and cell viability was determined by MTT assay. The values are represented as the percent viable cells where vehicle-treated cells were regarded as 100% viable. Data represents mean value of percent viable cells±S.E of three independent experiments.

FIG. 11 depicts quantitative representation of Lupeol induced apoptosis in LNCaP cells as assessed by flow cytometry. Cells were treated with Lupeol (5-30 µM). Cells showing fluorescence above that of control population, as indicated by the line in each histogram, are considered as apoptotic cells. The images shown here are representative of independent experiments with similar results. The values shown inside each graph indicates percent apoptotic cells.

Figure 12:
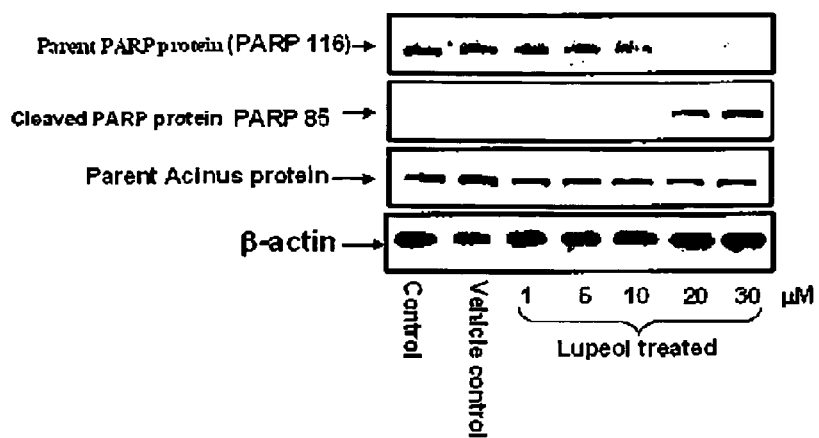

FIG. 12 depicts effect of Lupeol treatment on PARP cleavage and on protein expression of acinus, in LNCaP cells. Cells were treated with specified concentrations of Lupeol for 48 h, harvested and total cell lysates were prepared. PARP cleavage and the expression of acinus, were determined by western blot analysis. Equal loading was confirmed by stripping immunoblots and reprobing them for β-actin. The immunoblots shown here are representative of three independent experiments with similar results.

Figure 13:
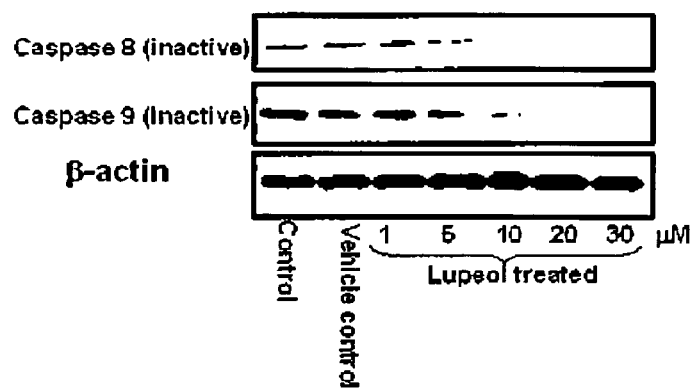

FIG. 13 depicts effect of Lupeol treatment on protein expression of pro-caspases-8 and -9 in LNCaP cells. Cells were treated with only specified concentrations of Lupeol for 48 h, harvested and total cell lysates were prepared. Expression of pro-caspases-8 and -9 were determined by western blot analysis. Equal loading was confirmed by stripping immunoblots and reprobing them for β-actin. The immunoblots shown here are representative of three independent experiments with similar results.

Figure 14:
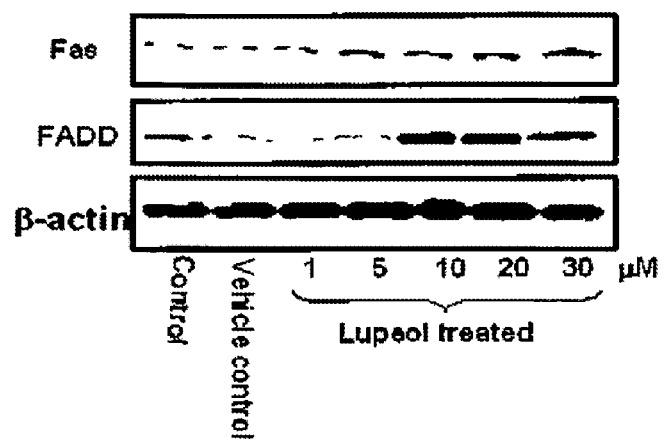

FIG. 14 depicts effect of Lupeol treatment on death receptor mediated apoptotic pathway in LNCaP cells: Cells were treated with vehicle (DMSO+alcohol) only or specified concentrations of Lupeol for 48 h, harvested and total cell lysates were prepared. The expression of death receptors including Fas and death adaptor proteins including FADD were determined by western blot analysis. Equal loading was confirmed by stripping immunoblots and reprobing them for β-actin. The immunoblots shown here are representative of three independent experiments with similar results.

Figure 15:
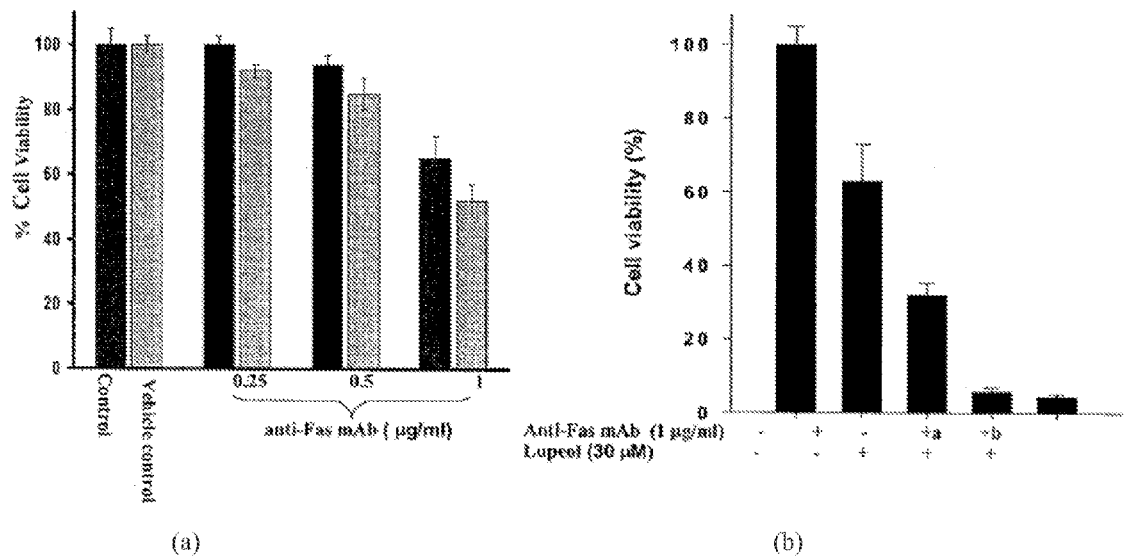

FIG. 15 depicts effect of Lupeol treatment in combination with anti-Fas mAb on the growth of LNCaP cells and on the expression of Fas receptor in LNCaP and PrEC cells: (a) Cells were treated with specified concentrations anti-Fas mAb for 48 h and cell viability was determined by MTT assay. The values are represented as the percent viable cells where vehicle-treated cells were regarded as 100% viable. Data represents mean value of percent viable cells±S.E of three independent experiments. V represents control and vehicle (DMSO) treated cells respectively. (b). Cells were treated with specified concentrations of Lupeol alone, anti-Fas mAb or with combination (Lupeol+anti-Fas mAb) for 48 h and cell viability was determined by MTT assay. "a" and "b" represent pre-treatment and co-treatment of cells with anti-Fas mAb respectively. The values are represented as the percent viable cells where vehicle-treated cells were regarded as 100% viable. Data represents mean value of percent viable cells±S.E of three independent experiments.

Figure 16:
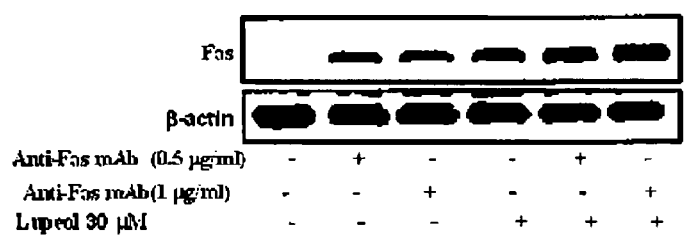

FIG. 16 depicts cells that were treated with vehicle (DMSO+alcohol) only or specified concentrations of Lupeol alone, anti-Fas mAb or with combination (Lupeol+anti-Fas mAb) for 48 h, harvested and total cell lysates were prepared. The expression of Fas receptor protein in total cell lysate was determined by western blot analysis. Equal loading was confirmed by stripping immunoblots and reprobing them for β-actin. The immunoblots shown here are representative of three independent experiments with similar results.

Figure 17:
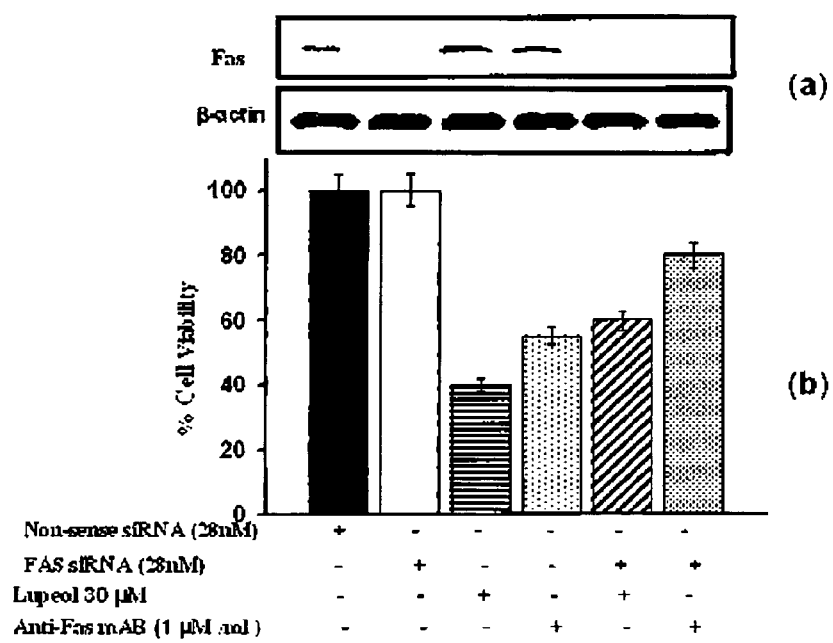

FIG. 17 depicts effect of Lupeol treatment on the growth of CaP cells transfected with Fas-siRNA and on the expression of Fas receptor in Fas-silenced CaP cells: (A). Cells were treated with specified concentrations of Lupeol alone, anti-Fas mAb or non-sense siRNA (negative control), Fas-siRNA, combination (Lupeol+Fas-siRNA) and combination (anti-Fas mAb+Fas-siRNA). The expression of Fas receptor protein in total cell lysate was determined by western blot analysis. Equal loading was confirmed by stripping immunoblots and reprobing them for β-actin. The immunoblots shown here are representative of three independent experiments with similar results. (B). Cells were treated with specified concentrations of Lupeol alone, anti-Fas mAb or non-sense siRNA (negative control), Fas-siRNA, combination (Lupeol+Fas-siRNA) and combination (anti-Fas mAb+Fas-siRNA). The values represent percent viable cells where vehicle-treated cells were regarded as 100% viable. Data represents mean value of percent viable cells±S.E of three independent experiments.

Figure 18:
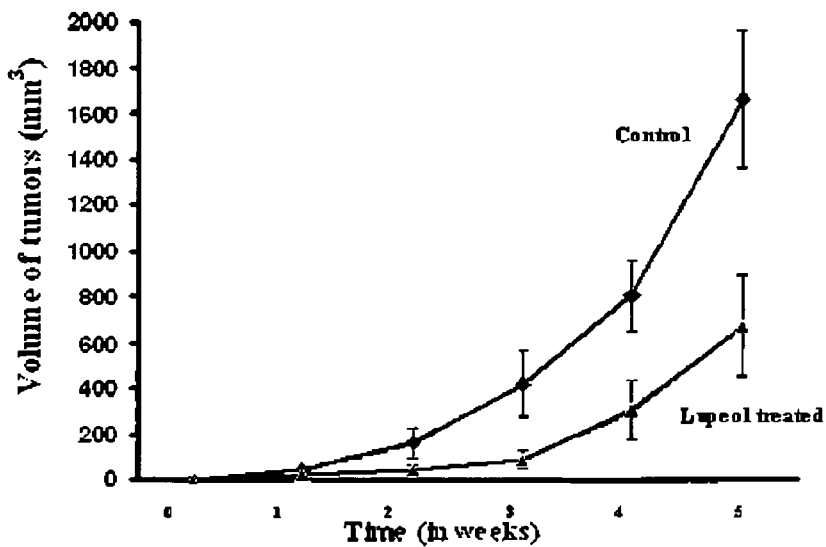

FIG. 18 depicts effect of lupeol treatment on the growth of tumors from CWR22Rv1 cells implanted in nude mice. The growth was measured in terms of average volume of tumors as a function of time. Data is represented as mean±SD. * indicates p<0.05 (B) Number of mice remaining with tumor volumes<1000 mm$^3$ after treatment with corn oil alone or Lupeol for indicated weeks. * indicates p<0.01

Figure 19:
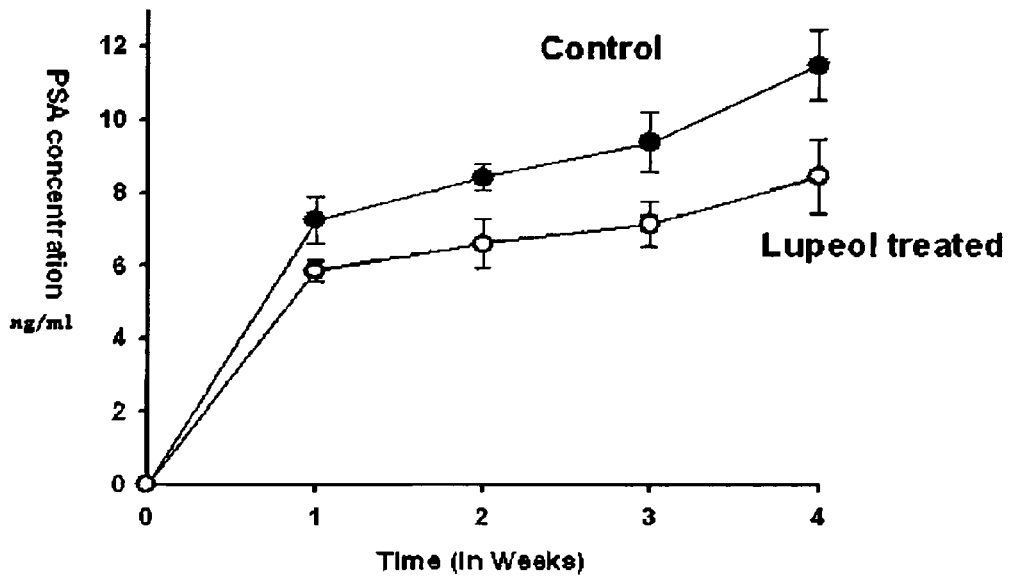

FIG. 19 depicts effect of Lupeol on human PSA levels in serum of athymic nude mice implanted with CWR22Rv1 cells. Data is represented as mean±SD. * indicates p<0.05.

Figure 20:
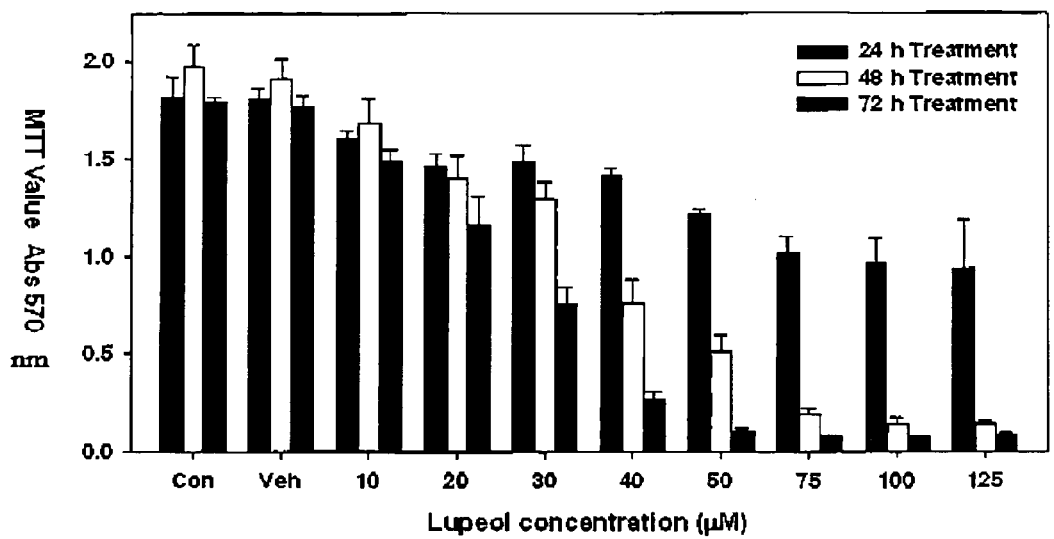

FIG. 20 depicts effect of Lupeol on viability of AsPC-1 cells. The cells were treated with specified concentrations of Lupeol for 24, 48 and 72 h, and cell viability was determined by MTT assay.

Figure 21:
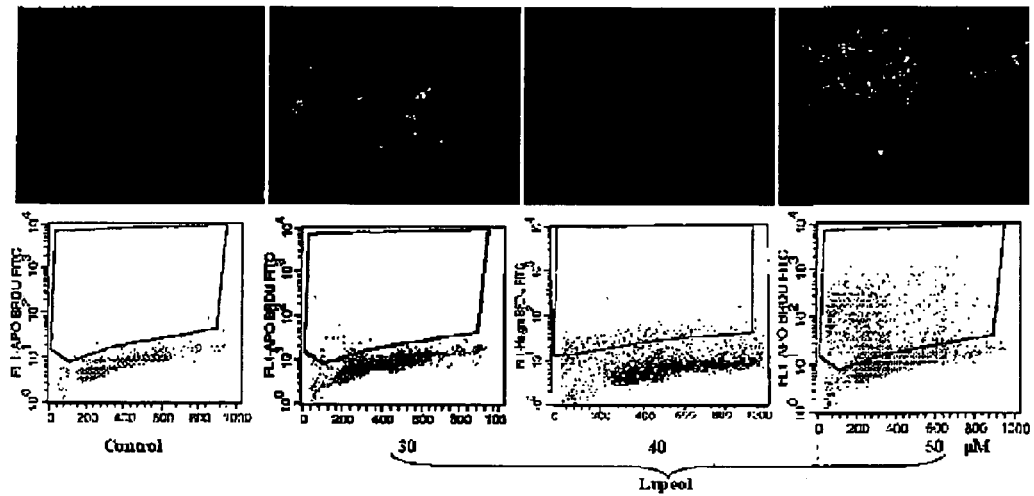

FIG. 21 depicts Lupeol induced apoptosis in AsPC-1 cells as assessed by fluorescence microscopy (Upper Panel) and by flow cytometry (Bottom Panel). Upper panel of FIG. 21 contains the representative micrographs of AsPC-1 cells undergoing apoptosis induced by treatment with Lupeol as assessed by fluorescence microscopy (Upper panel).

Figure 22:
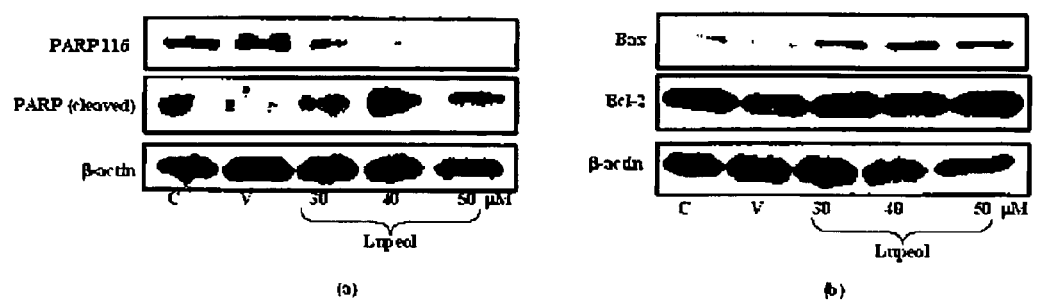

FIG. 22 depicts effect of Lupeol treatment on PARP cleavage and on protein expression of Bax, Bcl-2 in AsPC-1 cells.

Figure 23:
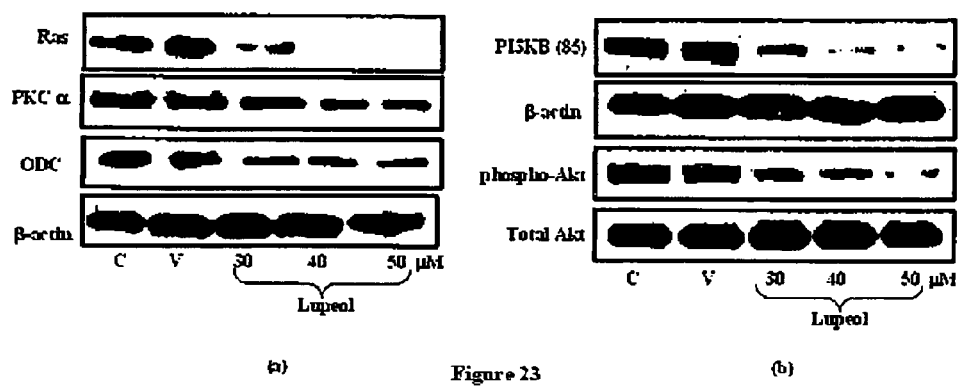

FIG. 23 depicts effect of Lupeol treatment on the expression of Ras, PKCα, ODC, PI3K (P85), pAkt and total Akt, p38 and Erk1/2 proteins in AsPC-1 cells.

FIG. 24 depicts effect of Lupeol treatment on the phosphorylation of I-κBα protein and p65-subunit of NFκB transcriptional factor in AsPC-1 cells.

FIG. 25 depicts effect of Lupeol treatment on the phosphorylation of p38 and Erk1/2 in MAP kinase signaling and p21 and Cyclin D-2 protein expression in AsPC-1 cells.

DETAILED DESCRIPTION OF THE INVENTION

General Description of the Invention

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

As defined herein, the term "isomer" includes, but is not limited to optical isomers and analogs, structural isomers and analogs, conformational isomers and analogs, and the like. In one embodiment, this invention encompasses the use of different optical isomers of an anti-tumor compound of Formula I. It will be appreciated by those skilled in the art that the anti-tumor compounds useful in the present Invention may contain at least one chiral center. Accordingly, the compounds used in the methods of the present invention may exist in, and be isolated in, optically-active or racemic forms. Some compounds may also exhibit polymorphism. It is to be understood that the present invention encompasses the use of any racemic, optically-active, polymorphic, or stereroisomeric form, or mixtures thereof, which form possesses properties useful in the treatment of tumor-related conditions described and claimed herein. In one embodiment, the anti-tumor compounds are the pure (R)-isomers. In another embodiment, the anti-tumor compounds are the pure (S)-isomers. In another embodiment, the compounds are a mixture of the (R) and the (S) isomers. In another embodiment, the compounds are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes the use of pharmaceutically acceptable salts of amino-substituted compounds with organic and inorganic acids, for example, citric acid and hydrochloric acid. The invention also includes N-oxides of the amino substituents of the compounds described herein. Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters. As used herein, the term "pharmaceutically acceptable salt" refers to a compound formulated from a base compound which achieves substantially the same pharmaceutical effect as the base compound.

This invention further includes method utilizing derivatives of the anti-tumor compounds. The term "derivatives" includes but is not limited to ether derivatives, acid derivatives, amide derivatives, ester derivatives and the like. In addition, this invention further includes methods utilizing hydrates of the anti-tumor compounds. The term "hydrate" includes but is not limited to hemihydrate, monohydrate, dihydrate, trihydrate and the like.

This invention further includes methods of utilizing metabolites of the anti-tumor compounds. The term "metabolite" means any substance produced from another substance by metabolism or a metabolic process.

As defined herein, "contacting" means that the anti-tumor compound used in the present invention is introduced into a sample containing the receptor in a test tube, flask, tissue culture, chip, array, plate, microplate, capillary, or the like, and incubated at a temperature and time sufficient to permit binding of the anti-tumor compound to a receptor. Methods for contacting the samples with the anti-tumor compound or other specific binding components are known to those skilled in the art and may be selected depending on the type of assay protocol to be run. Incubation methods are also standard and are known to those skilled in the art.

In another embodiment, the term "contacting" means that the anti-tumor compound used in the present invention is introduced into a subject receiving treatment, and the compound is allowed to come in contact in vivo.

As used herein, the term "treating" includes preventative as well as disorder remittent treatment. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

As used herein, the term "administering" refers to bringing a patient, tissue, organ or cells in contact with an anti-tumor compound according to Formula I. As used herein, administration can be accomplished in vitro, i.e. in a test tube, or in vivo, i.e. in cells or tissues of living organisms, for example, humans. In certain embodiments, the present invention encompasses administering the compounds useful in the present invention to a patient or subject. A "patient" or "subject", used equivalently herein, refers to a mammal, preferably a human, that either: (1) has a disorder remediable or treatable by administration of the anti-tumor compound according to Formula I; or (2) is susceptible to a disorder that is preventable by administering the anti-tumor compound according to Formula I.

As used herein, "pharmaceutical composition" means therapeutically effective amounts of the anti-tumor compound together with suitable diluents, preservatives, solubilizers, emulsifiers, and adjuvants, collectively "pharmaceutically-acceptable carriers." As used herein, the terms "effective amount" and "therapeutically effective amount" refer to the quantity of active therapeutic agent sufficient to yield a desired therapeutic response without undue adverse side effects such as toxicity, irritation, or allergic response. The specific "effective amount" will, obviously, vary with such factors as the particular condition being treated, the physical condition of the patient, the type of animal being treated, the duration of the treatment, the nature of concurrent therapy (if any), and the specific formulations employed and the structure of the compounds or its derivatives. In this case, an amount would be deemed therapeutically effective if it resulted in one or more of the following: (a) the prevention of skin disorder (e.g., skin cancer), prostate cancer or pancreatic cancer; and (b) the reversal or stabilization of skin disorder (e.g., skin cancer) prostate cancer or pancreatic cancer. The optimum effective amounts can be readily determined by one of ordinary skill in the art using routine experimentation.

Pharmaceutical compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, milamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

Also encompassed by the invention are methods of administering particulate compositions coated with polymers (e.g., poloxamers or poloxamines). Other embodiments of the compositions incorporate particulate forms protective coatings, protease inhibitors or permeation enhancers for various routes of administration, including topical, parenteral, pulmonary, nasal and oral. In one embodiment the pharmaceutical composition is administered parenterally, paracancerally, transmucosally, transdermally, intramuscularly, intravenously, intradermally, subcutaneously, intraperitonealy, intraventricularly, intracranially and intratumorally.

Further, as used herein "pharmaceutically acceptable carriers" are well known to those skilled in the art and include, but are not limited to, 0.01-0.1M and preferably 0.05M phosphate buffer or 0.9% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions administerable according to the invention include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Other embodiments of the compositions administered according to the invention incorporate particulate forms, protective coatings, protease inhibitors or permeation enhancers for various routes of administration, including parenteral, pulmonary, nasal and oral.

Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., in Enzymes as Drugs. (J. S. Holcerberg and j. Roberts, eds. pp. 367-383 (1981)); Katre, et al., "Chemical Modification of Recombinant Interleukin 2 by Polyethylene Glycol Increases it Potency in the Murine Meth A Sarcoma Model," Proc. Nat'l Acad. Sci., USA, 85:1487-1491 (1987); Newmark et al., 1982, J Appl Biochem, 4:185-9). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In yet another method according to the invention, a pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, i.e., the skin, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

The pharmaceutical preparation can comprise the anti-tumor compound alone, or can further include a pharmaceutically acceptable carrier, and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the anti-tumor compound can be administered to a subject by, for example, subcutaneous implantation of a pellet. In a further embodiment, a pellet provides for controlled release of anti-tumor compound over a period of time. The preparation can also be administered by intravenous, intraarterial, or intramuscular injection of a liquid preparation oral administration of a liquid or solid preparation, or by topical application. Administration can also be accomplished by use of a rectal suppository or a urethral suppository.

The pharmaceutical preparations administrable by the invention can be prepared by known dissolving, mixing, granulating, or tablet-forming processes. For oral administration, the anti-tumor compounds or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the anti-tumor compounds or their physiologically tolerated derivatives such as salts, esters, N-oxides, and the like are converted into a solution, suspension, or expulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Such compositions may be prepared as aerosols delivered to the nasopharynx or as injectables, either as liquid solutions or suspensions; however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like or any combination thereof.

In addition, the composition can contain minor amounts of auxiliary substances such as wetting or emulsifying agents, pH buffering agents which enhance the effectiveness of the active ingredient.

An active component can be formulated into the composition as neutralized pharmaceutically acceptable salt forms, Pharmaceutically acceptable salts include the acid addition salts, which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, drops, and the like, the anti-tumor compounds or their physiologically tolerated derivatives such as salts, esters, N-oxides, and the like are prepared and applied as solutions, suspensions, or emulsions in a physiologically acceptable diluent with or without a pharmaceutical carrier.

In another method according to the invention, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, N.Y., pp. 353-365 (1989); Lopez-Berestein ibid., pp. 317-327; see generally ibid).

For use in medicine, the salts of the anti-tumor compound may be pharmaceutically acceptable salts. Other salts may, however, be useful in the preparation of the compounds according to the invention or of their pharmaceutically acceptable salts. Suitable pharmaceutically acceptable salts of the compounds include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

In addition, the anti-tumor compounds described herein may be provided In the form of nutraceutical compositions where the anti-tumor compound prevents the onset of or reduces or stabilizes various deleterious skin disorders, e.g., skin cancer, prostate cancer or pancreatic cancer. The term "nutraceutical," or "nutraceutical composition", for the purposes of this specification, refers to a food item, or a part of a food item, that offers medical health benefits, including prevention and/or treatment of disease. A nutraceutical composition according to the present invention may contain only an anti-tumor compound according to the present invention as an active ingredient or, alternatively, may further comprise, in admixture with the aforesaid anti-tumor compound, dietary supplements including vitamins, co-enzymes, minerals, herbs, amino acids and the like which supplement the diet by increasing the total intake of that substance.

Therefore, the present invention provides methods of providing nutraceutical benefits to a subject comprising the step of administering to the subject a nutraceutical composition containing a compound having Formula I or a pharmaceutically acceptable salt thereof. Such compositions generally include a "nutraceutically-acceptable carrier" which, as referred to herein, is any carrier suitable for oral delivery including, but not limited to, the aforementioned pharmaceutically-acceptable carriers. In certain embodiments, nutraceutical compositions according to the invention comprise dietary supplements which, defined on a functional basis, include immune boosting agents, anti-arthritic agents, anti-inflammatory agents, anti-oxidant agents, anti-mutagenic agents, anti-malarial agents or mixtures thereof.

The immune boosters and/or anti-viral agents are useful for accelerating wound-healing and improved immune function; and they include extracts from the coneflowers, or herbs of the genus *Echinacea*, extracts from herbs of the genus *Sambuca*, and Goldenseal extracts. Herbs of the genus Astragalus are also effective immune boosters in either their natural or processed forms. Astragalus stimulates development into of stem cells in the marrow and lymph tissue active immune cells. Zinc and its bioactive salts, such as zinc gluconate and zinc acetate, also act as immune boosters in the treatment of the common cold.

Antioxidants include the natural, sulfur-containing amino acid allicin, which acts to increase the level of antioxidant enzymes in the blood. Herbs or herbal extracts, such as garlic, which contain allicin are also effective antioxidants. The catechins, and the extracts of herbs such as green tea containing catechins, are also effective antioxidants. Extracts of the genus Astragalus also show antioxidant activity. The bioflavonoids, such as quercetin, hesperidin, rutin, and mixtures thereof, are also effective as antioxidants. The primary beneficial role of the bioflavonoids may be in protecting vitamin C from oxidation in the body. This makes more vitamin C, or ascorbic acid, available for use by the body.

Bioflavonoids such as quercetin are also effective anti-inflammatory agents, and may be used as such in the inventive compositions. Anti-inflammatory herbal supplements and anti-inflammatory compounds derived from plants or herbs may also be used as anti-inflammatory agents in the inventive composition. These include bromolain, a proteolytic enzyme found in pineapple; teas and extracts of stinging nettle; turmeric, extracts of turmeric, or curcumin, a yellow pigment isolated from turmeric.

Another supplement which may be used in the present invention is ginger, derived from herbs of the genus *Zingiber*. This has been found to possess cardiotonic activity due to compounds such as gingerol and the related compound shogaol as well as providing benefits in the treatment of dizziness, and vestibular disorders. Ginger is also effective in the treatment of nausea and other stomach disorders.

Supplements which assist in rebuilding soft tissue structures, particularly in rebuilding cartilage, are useful in compositions for treating the pain of arthritis and other joint disorders. Glucosamine, glucosamine sulfate, chondroitin, and chondroitin sulfate are particularly useful for this purpose. Chondroitin may be derived from a variety of sources, such as Elk Velvet Antler. Marine lipid complexes, omega 3 fatty acid complexes, and fish oil are also known to be useful in treating pain associated with arthritis.

Supplements useful in treating migraine headaches include feverfew and *Gingko biloba*. The main active ingredient in feverfew is the sesquiterpene lactone parthenolide, which inhibits the secretion of prostaglandins which in turn cause pain through vasospastic activity in the blood vessels. Feverfew also exhibits anti-inflammatory properties. Fish oil, owing to its platelet-stabilizing and antivasospastic actions, may also be useful in treating migraine headaches. The herb *Gingko biloba* also assists in treatment of migraines by stabilizing arteries and improving blood circulation.

Although some of the supplements listed above have been described as to their pharmacological effects, other supplements may also be utilized in the present invention and their effects are well documented in the scientific literature.

The present invention provides numerous methods and pharmaceutical and nutraceutical compositions for treatment, inhibition, recurrence and occurrence of skin tumorigenesis, skin cancer related conditions, prostate cancer or pancreatic cancer. One preferred embodiment of the present invention provides a method for preventing skin, prostate or pancreatic tumorigenesis related conditions in a subject having those risks comprising the step of administering to the subject an effective amount of a compound having the formula:

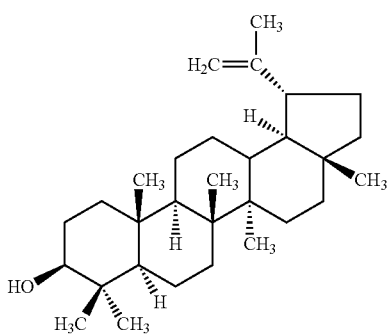

Tumorigenesis related conditions may include edema, hyperplasia, tumor, neoplasia, or combinations thereof. The compound further inhibits tumorigenesis in a dose dependent manner. The compound may be administered topically or intraperitoneally to the subject. The compound may also be administered in a pharmaceutically acceptable carrier, including an emollient or a patch. The compound further inhibits induction of ODC activity, ODC protein, COX-2 protein expression, iNOS protein expression, expression of catalytic and regulatory subunits of PI3K, phosphorylation of Akt, phosphorylation of IκB protein, activation of IKKα, activation and nuclear translocation of NFκB/p65, or NFκB DNA binding.

Another preferred embodiment of the present invention provides a method of preventing the occurrence or recurrence of skin, prostate or pancreatic cancer in a subject in risk thereof. The method comprises the step of administering to said subject an effective amount of (a) an anti-tumor compound having the structure:

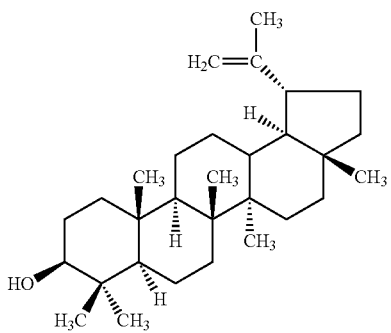

or
(b) a pharmaceutically acceptable salt of said compound. The compound further inhibits skin, prostate or pancreatic cancer in a dose dependent manner and may be administered topically to the subject. The compound may also be is administered in a pharmaceutically acceptable carrier, including an emollient or a patch. Further the compound inhibits induction of ODC activity, ODC protein, COX-2 protein expression, iNOS protein expression, expression of catalytic and regulatory subunits of PI3K, phosphorylation of Akt, phosphorylation of IκB protein, activation of IKKα, activation and nuclear translocation of NFκB/p65, or NFκB DNA binding. The occurrence or reoccurrence of skin, prostate or pancreatic cancer may include conditions such as edema, hyperplasia, tumor or neoplasia.

Yet another preferred embodiment of the present invention provides a pharmaceutical composition comprising (a) a compound having the formula:

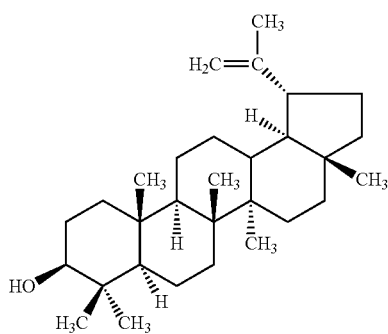

or (b) a pharmaceutically acceptable salt of said compound; and (c) a pharmaceutically-acceptable carrier. The compound may be available in a pharmaceutically acceptable carrier such as an emollient or a patch.

Yet another preferred embodiment of the present invention provides a method of providing nutraceutical benefits to a subject. The method comprises the step of administering to the subject a nutraceutical composition including (a) a compound having the formula:

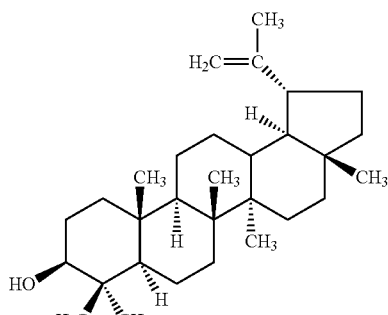

or (b) a pharmaceutically-acceptable salt of said compound; and (c) an acceptable carrier. The nutraceutical composition further comprises an immune boosting agent, anti-arthritic agent, anti-inflammatory agent, anti-oxidant anti-mutagenic agent, anti-malarial agent, or a mixture thereof.

Yet another preferred embodiment of the present invention includes a nutraceutical composition comprising: (a) a compound having the formula:

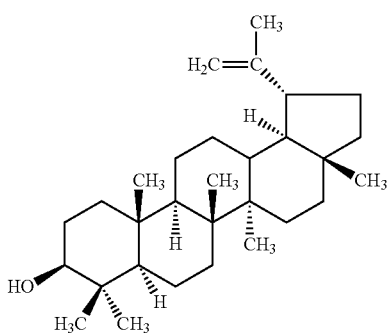

or (b) a pharmaceutically-acceptable salt of said compound; and (c) an acceptable carrier. The nutraceutical composition according further comprises an immune boosting agent, anti-arthritic agent, anti-inflammatory agent, anti-oxidant anti-mutagenic agent, anti-malarial agent, or a mixture thereof.

Yet another preferred embodiment of the present invention provides a pharmaceutical composition comprising (a) a compound having the formula:

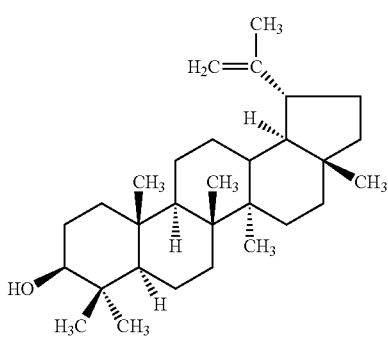

or (b) a pharmaceutically acceptable salt of said compound; and (c) a sunscreen lotion or cream. These sunscreen lotions or creams are commercially available and are well known to one of ordinary skill in the art. In a preferred embodiment, these lotions or creams may be used as an emollient by a subject, especially to avoid harmful exposure from ultraviolet radiation. Examples of commercially available sunscreen lotions and creams include PANAMA JACKS®, BANANA BOAT® and COPPERTONE®.

The following Examples are offered by way of illustration and not by way of limitation.

EXAMPLES

In view of the anti-inflammatory, anti-mutagenic and anti-oxidative activities of Lupeol, as well as its inhibitory potential against prostaglandin and cytokine production (Fernandez et al., 2001), the inventors explore that Lupeol may possess significant anti-tumor promoting potential.

I. Lupeol and Skin Cancer

In this study, the inventors assessed the anti-tumor promoting effect of Lupeol on CD-1 mouse skin and delineated the mechanism of its action.

Inhibitory Effect of Lupeol on TPA-Induced Cutaneous Edema:

Studies from the inventors' laboratory and by other have shown that TPA application to mouse skin results in cutaneous edema (Katiyar et at, 1996; Liang et at, 2002). In the present study, the inventors evaluated the protective effects of topical application of Lupeol in TPA-mediated cutaneous edema in CD-1 mouse. The inventors tested four doses 0.25, 0.5, 1 and 2 mg of Lupeol per animal in the inventors' preliminary studies. Since 0.25 and 0.5 mg of Lupeol did not exhibit any significant effect on primary biomarkers of tumor promotion (data not shown), therefore the inventors selected dose of 1 and 2 mg of Lupeol for further studies. The CD-1 mice were topically treated with Lupeol (1 and 2 mg/mouse) and 30 min later were topically treated with TPA (3.2 nmole/mouse). As determined by the weight of 1 cm diameter punch of the dorsal skin, application of TPA to CD-1 mouse skin resulted in a significant development of skin edema at 24 and 48 h post TPA-treatment compared to control and Lupeol treated groups (Table 1). At least four determinations were made at different dorsal skin sites per mouse in each group. The data represents the mean±SE of eight mice (*$p<0.01$ vs TPA). The skin application of Lupeol, 30 min prior to that of TPA application showed a significant protection against TPA-induced skin edema measured at 24 (48%; $p<0.01$) and 48 (43%; $p<0.01$) h post-treatment. The inventors found that topical application of Lupeol alone to mice did not result in an increase in skin edema at 24 and 48 h post treatment (Table 1).

TABLE 1

Inhibitory effect of topically applied Lupeol on TPA-induced cutaneous edema

| Treatments | Skin punch weight (mg/cm2) | | % protection | |
|---|---|---|---|---|
| | 24 hrs | 48 hrs | 24 hrs | 48 hrs |
| Control (vehicle alone) | 14.0 ± 1.0 | 15.0 ± 1.0 | | |
| Lupeol alone (2 mg) | 13.5 ± 1.5 | 15.5 ± 1.5 | | |
| TPA alone | 23.5 ± 0.5 | 25.5 ± 0.75 | | |
| TPA + Lupeol (1 mg) | 18.5 ± 1.0* | 20.0 ± 1.0* | 53 | 52 |
| TPA + Lupeol (2 mg) | 16.0 ± 1.5* | 16.5 ± 0.75* | 79 | 85 |

Figure 2:
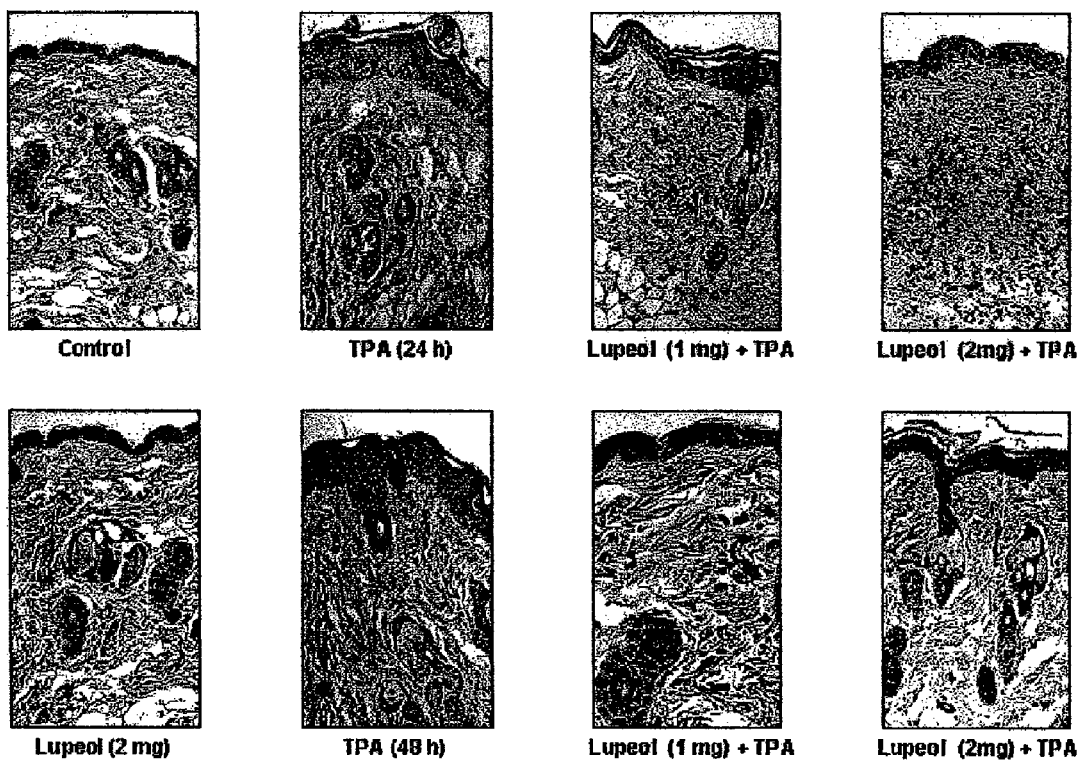
FIG. 2. Inhibitory effect of Lupeol on TPA-induced hyperplasia in CD-1 mice: 24 and 48 h after treatment, the animals were sacrificed; skin biopsies were processed for hematoxylin and eosin staining. Representative pictures are shown.

Inhibitory Effect of Lupeol on TPA-Induced Epidermal Hyperplasia:

The effect of topical application of Lupeol on TPA-mediated induction of epidermal hyperplasia was then assessed. As shown in FIG. 2, topical application of TPA resulted in an increase in epidermal hyperplasia at 24 and 48 h after treatment when compared to control treated animals. The topical application of Lupeol, however, prior to that of TPA application to mouse skin resulted in inhibition in the induction of epidermal hyperplasia (FIG. 2). Lupeol alone did not induce any epidermal hyperplasia as the histology of these animals was comparable to that of control mice (FIG. 2).

Figure 3:
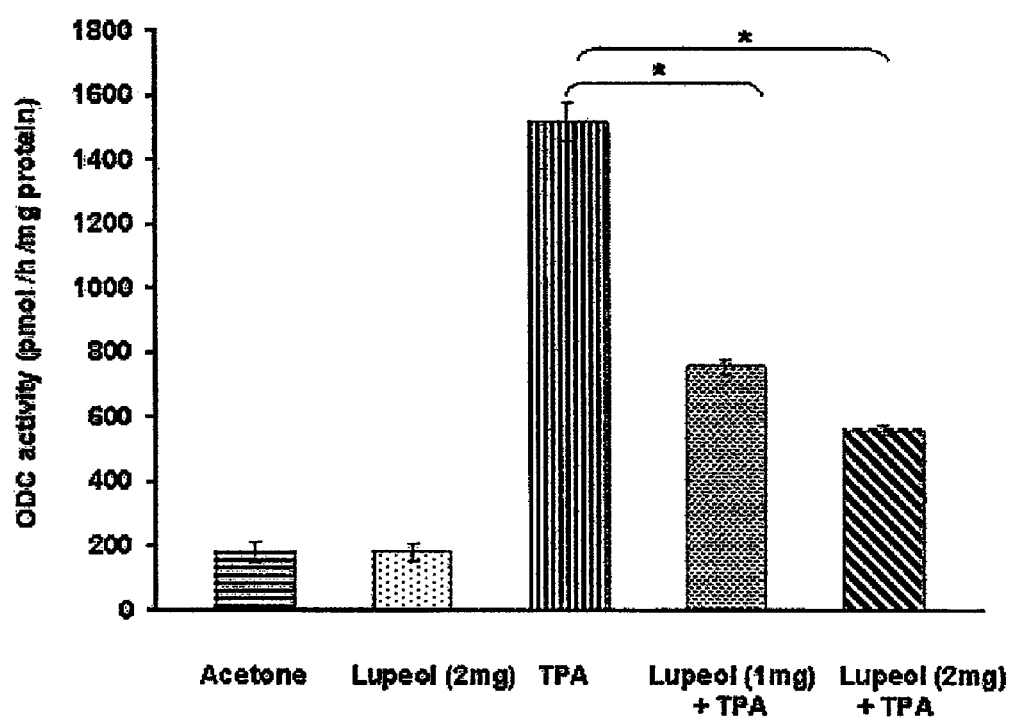
FIG. 3. Inhibitory effect of Lupeol on TPA-induced epidermal ODC activity: ODC enzyme activity was determined using 0.4 ml epidermal supernatant by measuring the release of $^{14}CO_2$ from the D, L-[$^{14}$C]ornithine. Data is represented as mean±SE of four individual values (* represents p<0.005). The epidermis from two animals was pooled for each determination.

Inhibition of TPA-Caused Induction of Epidermal ODC Activity by Lupeol:

In order to determine the effect of Lupeol against the TPA-induced ODC activity in CD-1 mice, groups of animals were treated topically with Lupeol (1 or 2 mg/animal, 30 min prior to topical application of TPA (3.2 nmol/animal). All the test substances were applied In 0.2 ml acetone. As shown in FIG. 3, pretreatment of animals with Lupeol resulted in a dose dependent inhibition of the TPA-caused induction of epidermal ODC activity. At the highest dose of Lupeol (2 mg/animal), used in this study, 75% inhibition ($p<0.005$) was observed as compared to TPA-treated control (FIG. 3). Lupeol at lower dose (1 mg/animal) also caused a substantial inhibition (50%; $p<0.005$) in the epidermal ODC activity in mice treated with TPA. Topical application of Lupeol alone (2 mg/animal) was without any effect on basal epidermal ODC activity.

Figure 4:
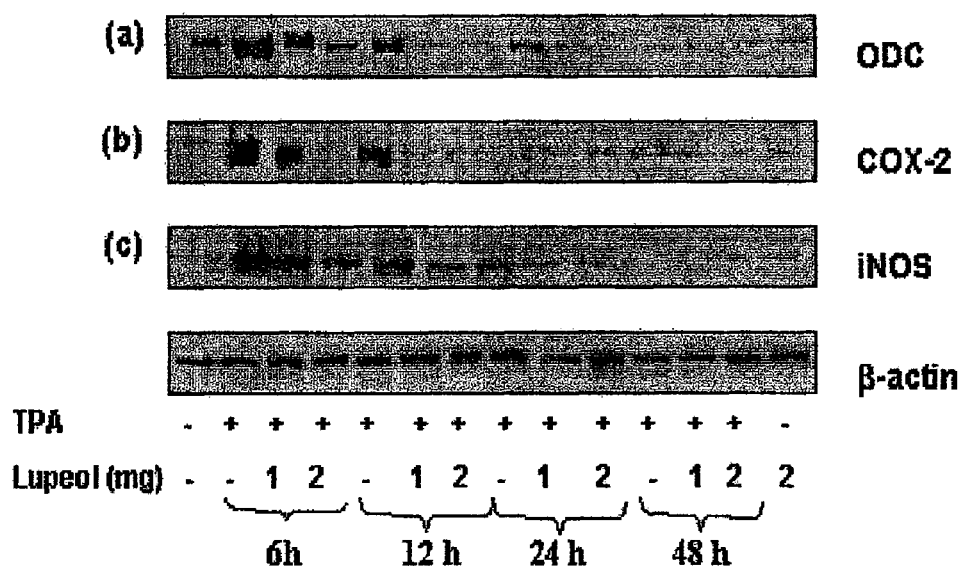
FIG. 4. Inhibitory effect of Lupeol on TPA-induced epidermal ODC, iNOS and COX-2 protein expression in CD-1 mice: At different times after treatment, the animals were sacrificed, epidermal protein lysate was prepared, and ODC and COX-2 protein expression were determined. Equal loading of protein was confirmed by stripping the immunoblot and reprobing it for β-actin. The immunoblots shown here are representative of three independent experiments with similar results. The values above each lane indicate relative density of the band normalized to β-actin.

Inhibition of TPA-Caused Induction of Epidermal ODC Protein Expression by Lupeol:

Next, the inventors assessed the effect of skin application of Lupeol on TPA-caused enhanced expression of ODC protein in the epidermis. Western blotting revealed that at 6 h post treatment of TPA, there was maximum expression of epidermal ODC protein expression and it gradually declined with the passage of time, i.e. at 12, 24 and 48 h post TPA treatment (FIG. 4a). Treatment of TPA caused a 4-fold increase in epidermal ODC protein level as compared to acetone treated control while pre-treatment of animals with Lupeol resulted in a significant inhibition against TPA-caused induction of epidermal ODC protein expression in a dose dependent manner at all time points investigated (FIG. 4a). Densitometric analysis of these blots indicated that, under experimental conditions used, the Inhibition varied from 50-70% in Lupeol-pretreated animals. Topical application of Lupeol alone up to 2 mg/animal was without any effect on enzyme level and did not cause any induction of epidermal ODC protein expression.

Inhibitory Effect of Lupeol on TPA-Induced Epidermal Cyclooxygenase (COX-2) and Induced Nitric Oxide Synthase (iNOS) Protein Expression:

COX-2 and iNOS are well established bio-markers of inflammation and tumor promotion. The inventors next assessed the effect of skin application of Lupeol on TPA-induced epidermal MOS and COX-2 protein expression. The inventors found that topical application of TPA to CD-1 mice resulted in an increase in epidermal COX-2 protein expression which was maximum (2.7-fold) at 6 h post TPA treatment when compared to the acetone treated control (FIG. 4b). The TPA-caused induction in the expression level of epidermal COX-2 gradually declined with the time i.e. at 12, 24 and 48 h post TPA-treatment. However, at all time points, the expression of COX-2 in mouse skin following TPA application remained higher than corresponding acetone treated control. At the lowest dose of Lupeol (1 mg/animal), there was 40% inhibition in TPA-caused increased epidermal COX-2 protein expression and the highest dose of Lupeol (2 mg/animal) restored the level of TPA-induced COX-2 protein almost to its basal level (FIG. 4b).

The inventors observed that topical application of TPA to CD-1 mice resulted in a significant increase in the expression of epidermal iNOS protein (FIG. 4c). The expression of iNOS was observed to reach its peak at 6 h post TPA treatment and it declined to its basal level at 12 h post TPA treatment. Topical application of TPA alone caused 5-fold increase in iNOS protein expression in mouse skin as compared to vehicle treated controls, however, pretreatment of Lupeol to the skin caused a dose dependent inhibition against TPA-caused increases of iNOS protein expression. Densitometric analysis of blots revealed that mice pretreated with Lupeol (2 mg/animal) showed 74% inhibition against TPA-induced epidermal iNOS protein expression (FIG. 4c). The application of Lupeol alone at the dose of 2 mg did not produce any change in epidermal COX-2 and iNOS protein expression when compared with vehicle-treated control animals.

Inhibitory Effect of Lupeol on TPA-Induced Epidermal Phosphatidyl Inositol Kinase (PI3K) and Phosphorylation of Akt:

Studies have shown that PI3K plays an important role in carcinogenesis (Luo et al., 2003; Mills et al., 2003; Osaki et al., 2004). The inventors next investigated whether TPA can induce PI3K protein expression in mouse skin. Western blot analysis revealed that topical application of TPA caused a significant (2 to 3-fold) increase in the expression of both catalytic (p110) as well as regulatory (p85) subunit of PI3K in mouse skin (FIGS. 5a & 5b). A 3-fold induction in the expression of catalytic subunit p110 was found at 6 h post TPA treatment only. There was a sustained induction upto 24 h post TPA treatment in the expression of regulatory subunit p85, with 6 h post TPA treatment showing the maximum expression. Topical application of Lupeol 30 min prior to TPA application resulted in a significant inhibition of TPA-induced increased expression of both catalytic and regulatory subunits of PI3K (FIGS. 5a & 5b). However there was no significant difference between control and treatments at later time points in the expression of catalytic p110 subunit. Skin application of animals with 2 mg Lupeol prior to TPA application resulted in the recovery of the expression of both p110 and p85 almost to their basal levels.

Several biological effects of PI3K are mediated through the activation (phosphorylation) of down stream target Akt. Akt also known as protein kinase B is a serine(Ser)/threonine (Thr) kinase, has been identified as an important component of pro-survival signaling pathway (Downward J, 1998). As Akt is a downstream substrate for PI3K, the inventors next assessed whether Akt is involved in cellular responses to TPA by performing western blot analysis with antibody to phosphorylated form of Akt at $Thr^{308}$, which is a prerequisite for the catalytic activity of Akt. Densitometric analysis of blots revealed a significant increase in the phosphorylation of Akt at $Thr^{308}$ in mouse skin treated with a single topical application of TPA (FIG. 5c). The inventors observed a maximum phosphorylation of Akt (3.8-fold) at 6 h post TPA treatment and this induction gradually declined with time after 12 h post TPA treatment. The inventors observed a dose dependent inhibition of TPA-induced phosphorylation of Akt at $Thr^{308}$ with the pre-application of Lupeol prior to TPA application in CD-1 mice skin (FIG. 5c). However no significant phosphorylation of Akt at $Thr^{308}$ was observed at 24 and 48 h time points in both control as well as treatment groups. Importantly, no change was observed in the total epidermal Akt content in mice treated with TPA as well as Lupeol as compared to vehicle treated control (FIG. 5d).

Inhibitory Effect of Lupeol on TPA-Induced Activation of NFκB and IKKα and Phosphorylation and Degradation of IκBα Protein Expression:

Studies have shown that Akt can promote survival by activating NFκB signaling pathway (Romashkova et al., 1999). Activation and nuclear translocation of NFκB is preceded by the phosphorylation and proteolytic degradation of IκBα (Israel, 1995). To determine whether the inhibitory effect of Lupeol was attributable to an effect on IκBα degradation, the inventors examined the cytoplasmic level of IκBα protein expression by western blot analysis. The inventors found that TPA application to mouse skin resulted in the degradation of IκBα protein expression at 12 and 24 h after treatment (FIG. 6a). There was no significant difference between control and treatments at 6 and 48 h in the expression of IκBα protein. Topical application of Lupeol 30 min prior to TPA application resulted in a significant inhibition of TPA-induced degradation of IκBα protein (FIG. 6a). The inventors next assessed whether TPA application affects the phosphorylation of IκBα protein. As shown by western blot, TPA-induced a marked increase in the phosphorylation level of IκBα protein at $Ser^{32}$ at 12 and 24 h post TPA treatment. Topical application of Lupeol prior to TPA application exhibited a dose dependent inhibition in TPA-induced phosphorylation of IκB protein (FIG. 6b). Studies have shown that IKKα activity is necessary for IκBα protein phosphorylation/degradation (Baldwin, 1996; Maniatis, 1997). To determine whether inhibition of TPA-induced IKKα activation by Lupeol is attributable to suppression of IκBα phosphorylation/degradation, the inventors also measured IKKα protein level. Densitometric analysis of the blots revealed that TPA application resulted in a 5.5-fold increase in the expression of IKKα protein that in turn phosphorylates and degrades IκBα protein (FIG. 6c). At 12 h post TPA treatment, IKKα protein expression was at its peak followed by a gradual decline in the induction of IKKα protein expression with time and no significant difference between control and treatments at 48 h in the expression of IKKα protein was observed. Topical application of Lupeol prior to TPA application dose dependently inhibited TPA-induced activation of IKKα and at the highest dose of Lupeol, there was almost 95% inhibition in TPA induced activation of IKKα protein at 12 h time point (FIG. 6c).

Next, the inventors investigated whether topical application of Lupeol inhibits TPA-induced activation and nuclear translocation of p65, the functionally active subunit of NFκB in mouse skin. As shown by western blot analysis, the inventors found that TPA application onto mouse skin resulted in the activation and nuclear translocation of NFκB/p65 (FIG. 7a). However, topical application of Lupeol prior to TPA application inhibited TPA-induced NFκB/p65 activation and nuclear translocation (FIG. 7a).

Inhibitory Effect of Lupeol on NFκB-DNA Binding Using EMSA:

The inventors next performed electrophoretic mobility shift assay (EMSA) to investigate the effect of Lupeol treatment on TPA-induced NFκB-DNA binding activity. As shown in FIG. 7b, TPA treatment resulted in a marked increase of NFκB-DNA binding activity in comparison to control and Lupeol groups (FIG. 7b). The induction of NFκB-DNA-binding activity coincided with the degradation of IκBα and activation of IKKα (FIG. 6c). Prior application of Lupeol to mouse skin significantly inhibited TPA-induced epidermal NFκB DNA binding activity (FIG. 7b).

Anti-Skin Tumor Promoting Effects of Lupeol:

Lupeol treatment for 28 weeks did not significantly affect the body weight gain of mice in any group and none of the treated mice exhibited any signs of toxicity (data not shown). Since application of 2 mg Lupeol to mice skin significantly inhibited various molecules that play significant role in the progression of skin tumors, the inventors selected this dose for assessing the anti-tumor promoting potential of Lupeol in DMBA-initiated mouse skin. As shown by data in FIG. 8, topical application of Lupeol prior to that of TPA in DMBA-initiated CD-1 mouse skin resulted in a significant inhibition of tumorigenesis. This Inhibition was evident when tumor data were considered as the percentage of mice with tumors (FIG. 8a), the number of tumors per mouse (FIG. 8b) and the number of tumors per group (FIG. 8c). At the termination of experiment at 28 weeks on test, compared with 100% animals with skin tumors in non-Lupeol treated group, only 53% of the animals exhibited the appearance of skin tumors. The tumor incidence data revealed that prior application of Lupeol to DMBA initiated and TPA treated mouse skin significantly increased the latency period of tumor formation ($p<0.05$, $\chi^2$ test). At the termination of the experiment at 28 weeks on test, compared with a total of 125 tumors in non-Lupeol treated group of animals, only 33 tumors in Lupeol treated group were recorded (FIG. 8b). Compared with the non-Lupeol treated group, such decrease in the total number of tumor in the Lupeol treated group correspond to 74% Inhibition. When these tumor data were considered in terms of number of tumors per mice, at the termination of the experiment at 28 weeks on test, compared with a 6.25 tumors per mouse in non-Lupeol treated group of animals, only 1.65 tumors per mouse in Lupeol treated group were recorded (FIG. 8c). Compared with the non-Lupeol treated group, such decrease in the number of tumor per mouse in the Lupeol treated group correspond to 74% inhibition.

Discussion

Cancer chemoprevention is increasingly being realized as an important area for cancer prevention, which, in addition to providing a practical approach of identifying potentially useful inhibitors of cancer development, also affords excellent opportunities to study the mechanisms of carcinogenesis (Conney et al., 1997; Bickers and Athar, 2000; Gupta and Mukhtar, 2002). The mouse skin model of multistage carcinogenesis has been a useful experimental framework to study basic mechanisms associated with the initiation, promotion and progression stages of carcinogenesis and defining newer chemopreventive agents. The intervention of cancer at the promotion stage appears to be most appropriate and practical. The major reason for this relates to the fact that tumor promotion is a reversible event at least in early stages, and requires repeated and prolonged exposure of a promoting agent (DiGiovanni, 1992; Surh, 2003). Further, tumor promotion is an obligatory step in the carcinogenic pathway where clonal expansion of initiated cell population occurs leading to what is referred as march of initiated cells towards malignancy. For this reason, it is important to identify mechanism-based effective novel anti-tumor-promoting agents. Accordingly, those agents, which have the ability to intervene at more than one critical pathway in the carcinogenic process, will have greater advantage over other single-target agents. Lupeol, a triterpene, is one such polyphenolic agent found in various edible plants such as olive, fig, mango and strawberry (Sosa, 1963; Anjaneyulu et al., 1982; Saeed and Sabir, 2002). Previously, it has been shown that Lupeol provides strong anti-oxidant protection against benzoyl peroxide induced toxicity in Swiss albino mouse skin (Saleem et al., 2001). Lupeol has been shown to significantly reduce the prostaglandin (PGE2) production and inhibit the production of TNFα and Interlukin-1β in vitro (Fernandez et al., 2001). Certain embodiments of the present invention established the chemopreventive potential of Lupeol, especially as shown in tumor model in CD-1 mice and provided comprehensive molecular mechanisms involved in this effect.

The topical application of TPA to mouse skin or its treatment in certain epidermal cells is known to result in a number of biochemical alterations, changes in cellular functions, and histological changes leading to skin tumor promotion (DiGiovanni, 1991; Katiyar et al., 1997; Katiyar and Mukhtar, 1997; Chun et al., 2002; Seo et al., 2003). The inventors' data clearly demonstrates that pre-application of Lupeol before TPA treatment affords significant inhibition of TPA-induced skin edema and hyperplasia (Table 1, FIG. 2). Previously, Lupeol has been reported to provide protection against croton oil induced edema in mouse ear and was reported to have more efficacy than indomethacin (Nikiema et al., 2001).

Accumulating information constantly reinforces that ODC, the first and the rate-limiting enzyme in the biosynthesis of polyamines plays an important role in the regulation of cell proliferation, differentiation and development of cancer (Thomas and Thomas, 2003). The induction of ODC has been suggested to play a significant role in tumor promotion. Studies with the mouse skin model showed an excellent correlation between the induction of ODC activity and the tumor-promoting ability of a variety of substances (Einspahr et al., 2003). It has been shown that over-expression of ODC is a sufficient condition for tumor promotion in mouse skin (Ahmad et al., 2001). Several lines of evidence indicate that aberrations in ODC regulation, and subsequent polyamine accumulation, are intimately associated with neoplastic transformation (Mohan et al., 1999). Elevated levels of ODC gene products are consistently detected in transformed cell lines, virtually all-animal tumors, and in certain tissues predisposed to tumorigenesis (Auvinen et al., 1997). Because tumor formation can be prevented by the agents that block induction of ODC (Verma et al., 1979; Nakadate et al., 1985), ODC inhibition was shown to be a promising tool for screening inhibitors of tumorigenesis. In the present study, topical application of Lupeol prior to that of TPA resulted in a significant inhibition of TPA-mediated induction of epidermal ODC activity (FIG. 2). It is reasonable to believe that Lupeol application inhibited the action of the tumor promoter and/or the enzymatic pathway(s) that regulates the ODC induction rather than interacting directly with the enzyme. In addition, the inventors' data obtained from western blot analysis demonstrate that prior application of Lupeol to that of TPA showed an inhibitory effect of Lupeol against TPA induced increases in the levels of epidermal ODC protein in mouse. The magnitude of the inhibitory effect of topical application of Lupeol on TPA-induced increases in ODC protein expression seem to be similar to that for inhibition of TPA-induced increases in ODC enzyme activity.

Tumor promotion is closely linked to inflammation and oxidative stress, and it is likely that compounds that have anti-inflammatory and anti-oxidative properties act as anti-tumor promoters as well (Bhimani et al., 1993). Cyclooxygenase isoform (COX-2) and iNOS are important enzymes involved in mediating the inflammatory process (Herschman, 1994; Smith et al., 1996). COX-2 and iNOS have been reported to play an important role in cutaneous inflammation, cell proliferation, and skin tumor promotion (Furstenberger and Marks, 1985; Herschman, 1994). There is considerable body of compelling evidence that inhibition of COX-2 and iNOS expression or activity is important for not only alleviating inflammation, but also for prevention of cancer (Kim et al., 2003). In this study the inventors showed the inhibitory effects of Lupeol against TPA-caused induction of epidermal COX-2 and iNOS protein expression in CD-1 mouse (FIG. 3). These inhibitory effects also correlate with the inhibitory effect of Lupeol against TPA-caused induction of skin edema (Table 1) and hyperplasia (FIG. 2). These inhibitory effects of Lupeol against TPA-mediated responses in the mouse skin suggest that the primary effect of Lupeol may be against inflammatory responses, which may then result in inhibition of tumor promotion.

Figure 5:
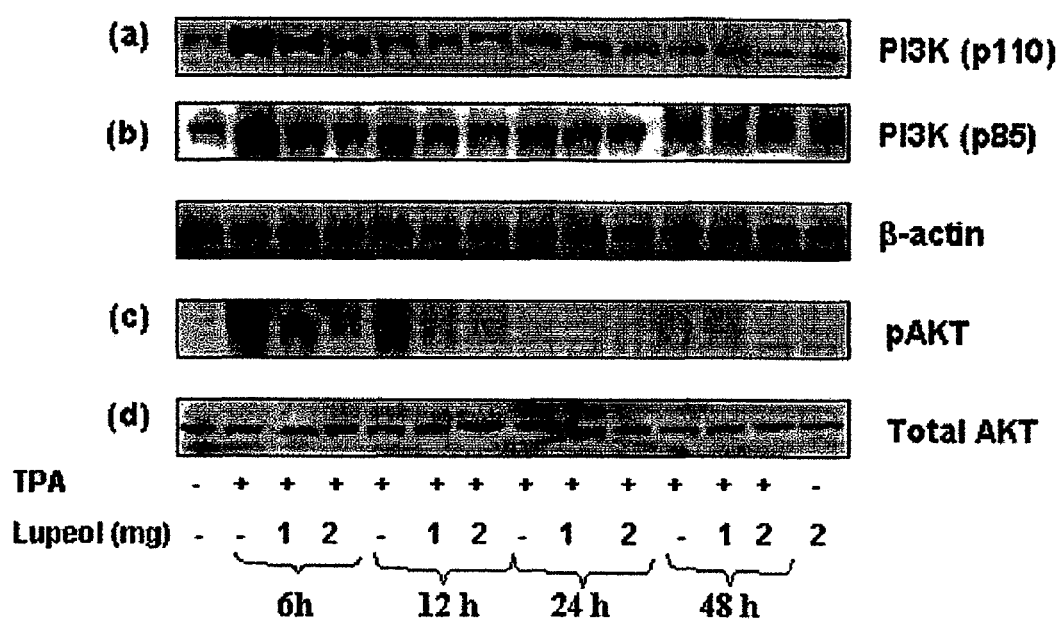
FIG. 5. Inhibitory effect of Lupeol on TPA-induced activation of PI3K and phosphorylation of Akt in CD-1 mice: At different times after treatment, the animals were sacrificed, epidermal protein lysate was prepared, and PI3K and phosphorylated (Thr$^{308}$) Akt and total Akt protein expression were determined. The immunoblots shown here are representative of three independent experiments with similar results. The values above each lane indicate relative density of the band normalized to β-actin.

Recent reports indicate that well known biomarkers of tumor promotion and inflammation i.e. COX-2, iNOS and ODC are regulated by NFκB transcriptional factor (Callejas et al., 1999). NFκB molecule, in addition to regulation by IκBα molecule, is also reported to be regulated by PI3K/Akt signaling pathway (Carpenter and Cantley, 1996). Both NFκB and PI3K/Akt signaling pathways have emerged as promising molecular targets in the prevention of cancer. Since Lupeol significantly inhibited the induction of ODC, COX-2 and iNOS, the inventors investigated if Lupeol exerts effects on these molecules or interferes with the signaling molecules that regulate them. Therefore, the inventors investigated the efficacy of Lupeol in the modulation of molecules involved in NFκB and PI3K/Akt signal pathway. PI3K/Akt are important regulatory molecules that are involved in different signaling pathways and in the control of cell growth, promote cell survival, and malignant transformation (Carpenter and Cantley, 1996; Stambolic et al., 1999). The inventors' study clearly demonstrated that topical application of TPA resulted in the activation of both regulatory subunit (p85) and catalytic subunit (p110) of PI3K and phosphorylation of Akt at Thr$^{308}$protein expression as an early event (FIG. 5). Topical application of Lupeol prior to TPA application to mouse skin resulted in reduction in TPA-induced expression of PI3K and phosphorylation of Akt (FIG. 5). The PI3K/Akt promotes cell survival by activating NFκB signaling pathway (Romashkova and Makarov, 1999). Upon phosphorylation and subsequent degradation of IκB, NFκB activates and translocates to the nucleus (Bours et al., 2000). Several lines of evidence suggest that proteins from the NFκB and IκB families are involved in carcinogenesis. NFκB controls the expression of several growth factors, oncogenes and tumor suppressor genes (c-myc, p53), genes encoding cell adhesion proteins (ICAM-1, ELAM-1, VCAM-1) and proteases of the extracellular matrix (Epinat and Gilmore, 1999). NFκB is activated by various stimuli, including growth factors, carcinogens and tumor promoters including TPA (Ahmad et al., 2000; Afaq et al., 2003). Studies have shown that NFκB activity affects cell survival and determines the sensitivity of cancer cells to cytotoxic agents as well as ionizing radiation (Epinat and Gilmore, 1999). In the present study, the inventors have demonstrated that topical application of TPA to mouse skin resulted in activation and nuclear translocation of NFκB (FIG. 7).

The IKK complex is believed to be an important site for integrating signals that regulate the NFκB pathway. In the present study, the inventors observed that TPA application to mouse skin resulted in an increased expression of IKKα, and phosphorylation and degradation of IκBα protein (FIG. 6). Interestingly, the inventors found that topical application of Lupeol prior to TPA application to mouse skin inhibited TPA-induced NFκB, IKKα activation, and phosphorylation and degradation of IκBα protein (FIGS. 6 & 7). Phosphorylation of IκBα an inhibitory subunit of NFκB, on serine residues 32 and 36 by kinases (IKK), precedes rapid degradation of IκBα that in turn activates NFκB (Baldwin, 1996; Maniatis, 1997). It is only when IκBα is degraded that NFκB is transported into the nucleus (Baeuerle and Baltimore, 1996). Because Lupeol inhibits IκBα phosphorylation and degradation, the inventors' study suggests that the effect of Lupeol on NFκB/p65 is through inhibition of phosphorylation and subsequent proteolysis of IκBα.

The results in FIG. 8 show the protective effects of skin application of Lupeol on TPA-caused tumor promotion in DMBA-initiated CD-1 mouse skin. The pre-application of Lupeol to mice skin showed protective effects when tumor data were considered as the total number of tumors or tumors per mouse and the percent mice bearing tumors (FIG. 8). These chemopreventive and anti-tumor promotion effects in murine skin by Lupeol can be explained by the biochemical mechanisms observed in the present study. Based on the outcome of this study, the inventors suggest multiple pathways by which Lupeol results in the inhibition of tumor promotion in mouse skin. This may be explained by modulation of NFκB mediated by PI3K/Akt that in turn affects COX-2 and INOS. Lupeol may inhibit ODC activity via modulating NFκB or some other pathway regulating ODC gene. Lupeol seems to act as a modulating agent in multiple signaling pathways, thus proving as an excellent example of being an ideal chemopreventive agent.

In various embodiments of the present invention, the inventors have shown that topical application of Lupeol prior to TPA application to CD-1 mice resulted in a significant decrease in skin edema, hyperplasia, epidermal ODC activity and protein expression of ODC, iNOS and COX-2, classical markers of Inflammation and tumor promotion. In addition, the inventors have also shown that topical application of Lupeol prior to TPA application also resulted In inhibition of activation of PI3K and phosphorylation of Akt, activation of NFκB/p65 and IKKα, and degradation and phosphorylation of IκBα. In addition the inventors showed that pre-application of Lupeol inhibited skin tumorigenesis in CD-1 mice.

The inventors' data clearly demonstrate that Lupeol could be a potent anti-tumor promoting agent because it inhibits TPA-induced tumor promotion in an in vivo animal model. Chemopreventive agents such as Lupeol may be used in an emollient or patch for chemoprevention or treatment of skin cancer, for example in combination with a sunscreen lotion that is commercially available. In addition, because Lupeol exerts multiple effects on biomarkers associated with carcinogenesis, it may be tested for the cancer chemoprevention of other organs.

Materials and Methods

Materials: ODC, iNOS, COX-2, TNFα, IKKα anti-bodies were procured from Santa Cruz Biotechnology, Inc. (Santa Cruz, Calif., USA). IκBα and IκBα (phospho) antibodies were obtained from Cell Signaling Technology, (Beverly, Mass., USA). AKT and PI3K were purchased from Upstate, (Lake Placid, N.Y., USA). NFκB/p65 antibody was procured from Geneka Biotechnology Inc. (Montreal, Canada). Anti-mouse or anti-rabbit secondary antibody horse-radish peroxidase conjugate was obtained from Amersham Life Science Inc. (Arlington Height, Ill., USA). Lupeol, DMBA (7, 12, dimethyl benz(a)anthracene) and TPA (12-O-tetradecanoyl-phorbol acetate) were purchased from Sigma Chemicals (St. Louis, Mo., USA). Lightshift™ chemiluminescent EMSA kit was obtained from Pierce (Rockford, Ill., USA). The DC BioRad Protein assay kit was purchased from BioRad Laboratories (Herculus, Calif.). Novex pre-cast Tris-Glycine gels were obtained from Invitrogen (Carlsbad, Calif., USA).

Animals:

Female CD-1 mice (5-6 weeks old) were obtained from Charles River Laboratories (USA). These mice were housed four per cage under standard animal house conditions with a 12-h light/12-h dark cycle, and housed at 24±2° C. and 50±10% relative humidity. Animals were fed a Purina chow diet and water ad libitum.

Treatment of Animals for Short-Term Studies:

The animals were shaved on the dorsal side of the skin, divided into four groups and treated topically on the shaved area with either 0.4 ml vehicle (acetone), or TPA (3.2 nmol/0.4 ml acetone/animal, v/v), or Lupeol (1 or 2 mg/0.2 ml acetone/animal, w/v) followed 30 min later with TPA (3.2 nmol/0.2 ml acetone/animal). Animals were sacrificed at different times point i.e. 6, 12, 24 and 48 h post TPA treatment. The epidermis was separated from the whole skin and homogenized in 0.1 M Tris-HCl buffer (pH 7.2) using a Polytron tissue homogenizer (Brinkmann Instruments, Westbury, N.Y., USA) at 100,000×g supernatant, and microsomal fractions were prepared as described earlier (Katiyar and Mukhtar, 1997). The sample of 6 h treatment group was used to assess the ODC activity as this time point has previously been shown for optimal induction of the enzyme (Katiyar er al., 1996).

Edema and Hyperplasia:

To assess the inhibitory effect of pre-application of Lupeol on TPA-induced edema, 1 cm-diameter punches of skin from vehicle-, Lupeol-, TPA- or Lupeol- and TPA-treated mice were removed, made free of fat pads, and weighed immediately. After drying for 24 h at 50° C., the skin punches were reweighed, and the loss of water content was determined. The difference in the amount of water gain between the control (vehicle treated) and TPA treated represented the extent of edema induced by TPA, whereas that between the control vehicle and Lupeol plus TPA represented the inhibitory effect of Lupeol. For the hyperplasia study, skin was removed, fixed in 10% formalin, and embedded in paraffin. Vertical sections (5 μm) were cut, mounted on a glass slide, and stained with hematoxylin and eosin.

ODC Enzyme Activity:

ODC enzyme activity was determined using 0.4 ml epidermal supernatant by measuring the release of $^{14}CO_2$ from the D, L-[$^{14}$C] ornithine as reported earlier. (Gupta et al., 1999). The epidermis from the skin was homogenized at 4° C. in a glass-to-glass homogenizer in 10 volumes of ODC buffer [50 mM Tris-HCl buffer (pH 7.5) containing 0.1 mM EDTA, 0.1 mM dithiothreitol, 0.1 mM pyridoxal-5-phosphate, 1 mM 2-mercaptoethanol and 0.1% Tween-80]. The homogenate was centrifuged at 100,000×g at 4° C. and the supernatant was used for enzyme determination. Briefly, 100 μl of the supernatant was added to 0.25 ml of the assay mixture [35 mM sodium phosphate (pH 7.2), 0.2 mM pyridoxal phosphate, 4 mM dithiothreitol, 1 mM EDTA, 0.4 mM L-ornithine containing 0.5 μl of DL-[1-$^{14}$C] ornithine hydrochloride] in 15 ml corex centrifuge tube equipped with rubber stoppers and central well assemblies containing 0.2 ml ethanolamine and methoxyethanol in 2:1 (v/v) ratio. After incubation at 37° C. for 60 min, the reaction was terminated by the addition of 0.5 ml of 2 M citric acid, using a 21 G needle/syringe. The incubation was continued for 1 h. Finally, the central well containing the ethanolamine: methoxyethanol mixture to which $^{14}CO_2$ has been trapped was transferred to a vial containing 10 ml of toluene-based scintillation fluid and 2 ml of ethanol. The radioactivity was measured in a Beckman LS 6000 SC liquid scintillation counter. Enzyme activity was expressed as pmol $CO_2$ released/h/mg protein.

Preparation of Cytosolic and Nuclear Lysates:

Epidermis from the whole skin was separated as described earlier (Katiyar et al., 1999) and was homogenized in ice-cold lysis buffer [50 mM Tris-HCl, 150 mM NaCl, 1 mM EGTA, 1 mM EDTA, 20 mM NaF, 100 mM $Na_3VO_4$, 0.5% NP-40, 1% Triton X-100, 1 mM PMSF (pH 7.4)] with freshly added protease inhibitor cocktail, Protease Inhibitor Cocktail Set III (Calbiochem, La Jolla, Calif., USA). The homogenate was then centrifuged at 14,000×g for 25 minutes at 4° C. and the supernatant (total cell lysate) was collected, aliquoted and stored at −80° C. For the preparation of nuclear lysate, 0.2 g of the epidermis was homogenized in 1 ml of ice-cold phosphate-buffered saline (pH 7.6) and centrifuged at 12,000×g for 5 min at 4° C. The pellet was resuspended in 1 ml of cold buffer containing 10 mM HEPES (pH 7.9), 2 mM $MgCl_2$, 10 mM KCl, 1 mM dithiothreitol, 0.1 mM EDTA and 0.1 mM PMSF. After homogenization in a tight-fitting Dounce homogenizer, the homogenates were left on ice for 10 min and centrifuged at 25,000×g for 10 min. The nuclear pellet was resuspended in 0.1 ml of the buffer containing 10 mM HEPES (pH 7.9), 300 mM NaCl, 50 mM KCl, 0.1 mM EDTA, 1 mM dithiothreitol, 0.1 mM PMSF, and 10% glycerol with freshly added protease inhibitor cocktail (Protease Inhibitor Cocktail Set III, Calbiochem, La Jolla, Calif.). The suspension was gently shaken for 20 min at 4° C. After centrifugation at 25000×g for 10 min, the nuclear extracts (supernatants) were collected and quickly frozen at −80° C. The protein content in the lysates was measured by DC BioRad assay (BioRad Laboratories, Hercules, Calif.) as per the manufacturer's protocol.

Western Blot Analysis:

For western blot analysis, 40 μg of the protein was resolved over 8-12% polyacrylamide gels and transferred to a nitrocellulose membrane. The blot containing the transferred protein was blocked in blocking buffer (5% nonfat dry milk, 1% Tween 20; in 20 mM TBS, pH 7.6) for 1 h at room temperature followed by incubation with appropriate primary antibody in blocking buffer for 1 h to overnight at 4° C. This was followed by incubation with anti-mouse or anti-rabbit secondary antibody horse-radish peroxidase (Amersham Life Sciences, Inc., USA) for 1 h and then washed several times and detected by chemiluminescence ECL kit, (Amersham Life Sciences, Inc., USA) and autoradiography using XAR-5 film obtained from Eastman Kodak Co. (Rochester, N.Y., USA). Densitometric measurements of the band in western blot analysis were performed using digitalized scientific software program UN-SCAN-IT (Silk Scientific Corporation, Orem, Utah, USA).

Electrophoretic Mobility Shift Assay (EMSA).

EMSA for NFκB was performed using Lightshift™ chemiluminescent EMSA kit (Pierce, Rockford, Ill., USA) by following the manufacturer's protocol. To start with, DNA was biotin labeled using the Biotin 3' end labeling kit (Pierce, Rockford, Ill., USA). Briefly, in a 50 μl reaction buffer, 5 pmol of double stranded NFκB oligonucleotide 5'-AGT TGA GGG GAC TTY CCC AGG C-3'; 3'-TCA ACT CCC CTG AAA GGG TCC G-5' was incubated in a microfuge tube with 10 μl of 5×TdT (terminal deoxynucleotidyl transferase) buffer, 5 μl of 5 μM biotin-N4-CTP, 10 U of diluted TdT, 25 μl of ultrapure water and incubated at 37° C. for 30 min. To extract labeled DNA, 50 μl of chloroform:isoamyl alcohol (24:1) was added to each tube and centrifuged briefly at 13,000×g. The top aqueous phase containing the labeled DNA was removed and saved for binding reactions. Each binding reaction contained 1×-binding buffer (100 mM Tris, 500 mM KCl, 10 mM Dithiothretol, pH 7.5), 2.5% glycerol, 5 mM $MgCl_2$, 50 ng/μl poly (dI-dC), 0.05% NP-40, 5 μg of nuclear extract and 20-50 fmoles of biotin-end labeled target DNA. The content was incubated at room temperature for 20 min. To this reaction mixture, was added 5 μl of 5× loading buffer, subjected to gel electrophoresis' on a native polyacrylamide gel and transferred to a nylon membrane. When the transfer was complete DNA was cross-linked to the membrane at 120 $mJ/cm^2$ using a UV cross-linker equipped with 254 nm bulbs. The biotin end-labeled DNA was detected using streptavidin-horseradish peroxidase conjugate and a chemiluminescent substrate. The membrane was exposed to X-ray film (XAR-5 Amersham Life Science Inc., Arlington Height, Ill., USA) and developed using a Kodak film processor.

Skin Tumorigenesis:

Female CD-1 mice were used in DMBA- and TPA-induced, two-stage skin tumorigenesis protocol as described earlier (Katiyar et al., 1996). The dorsal side of the skin was shaved using electric clippers, and the mice with hair cycles in the resting phase were used for tumor studies. In each group, 20 animals were used. Tumorigenesis was initiated in the animals by a single topical application of 200 nmol DMBA in 0.2 ml vehicle on the dorsal shaved skin, and 1 week later, the tumor growth was promoted with twice-weekly applications of 3.2 nmol TPA in 0.2 ml vehicle. To assess its anti-skin tumor-promoting effect, Lupeol at a dose of 2 mg/animal, which produced significant inhibition against TPA-caused induction of ODC, was applied topically 30 min prior to each TPA application in different groups. Treatment with TPA alone or Lupeol plus TPA was repeated twice weekly up to the termination of the experiments at 28 weeks. Animals in all the groups were watched for any apparent signs of toxicity, such as weight loss or mortality during the entire period of study. Skin tumor formation was recorded weekly, and tumors larger than 1 mm in diameter were included in the cumulative number only if they persisted for 2 weeks or more.

Statistical Analysis

A two-tailed Student's t test was used to assess the statistical significance between the TPA treated and Lupeol+TPA treated groups. A p value<0.05 was considered statistically significant. In tumorigenesis experiments, the statistical significance of difference between TPA and Lupeol+TPA groups was evaluated by the Wilcoxon rank sum test and $\chi^2$ analysis.

II. Lupeol and Prostate Cancer

In prostate cancer (CaP) a fine balance between cell proliferation and apoptotic death is lost resulting in increased cellular mass and tumor progression. One approach to redress this imbalance and control this malignancy is its preventive intervention through use of dietary natural agents. Lupeol, a triterpene, is a potent anti-inflammatory agent and recently we have shown that it is an effective anti-tumor promoting agent in mouse skin tumor model (Saleem et al, Oncogene, 23: 5203-5214, 2004). Here, the inventors investigated the growth-inhibitory effect and associated mechanisms of Lupeol in androgen-dependent human prostate carcinoma LNCaP cells. Lupeol (5-30 μM) treatment resulted in significant inhibition of cell viability at 48 and 72 h post treatment in a time and dose dependent manner. Flow cytometric and immunoblot studies revealed that Lupeol mediated cell death was due to apoptosis. Lupeol was found to induce the cleavage of PARP protein and degradation of Acinus protein with no change in Bcl2, Bax and Caspase 7 protein expression suggesting involvement of a mitochondria-independent apoptotic pathway. In Lupeol treated cells, an increase in the expression of FADD protein was observed. Since FADD acts as an adapter protein for many death inducing signaling molecules such as TNFR-1, APO-3, DR-5, and FAS receptor proteins, expression levels to establish Lupeol specificity was determined. Lupeol caused a significant increase in the expression of FAS receptor protein with no change in the protein expression of TRADD and TNFR-1, APO-3 and DR-5 receptors. In addition, no significant change in the expression of cell death-inducing receptor ligands such as FAS-L, APO-3L and TRAIL was observed. In parallel experiments, treatment of cells with a combination of a Fas-agonist and Lupeol resulted in an increased cell death as compared to the additive effect of the two compounds alone, suggesting a synergistic effect. A possible explanation for this observation could be that Lupeol might be directly activating FAS protein. Next, we determined whether Lupeol could Inhibit the CaP cell tumor growth in an athymic nude mouse xenografts model. The mice were implanted with androgen-dependent CWR22Rv1 cells and received an i.p. injection of Lupeol (1 mg/animal) three times a week. A significant reduction in tumor growth was observed in Lupeol treated mice as compared with untreated control. Taken together, these molecular alterations provide an insight into Lupeol-caused growth inhibition and apoptotic death of human CaP cells. Because early clinical CaP growth is an androgen-dependent response, the results of the present study employing androgen-dependent LNCaP cells suggest that Lupeol has promise and potential to be an effective agent against CaP.

Generally, Lupeol Induces apoptotic cell death of androgen-dependent prostate cancer cells (LNCaP) and inhibits the tumorigenicity of androgen-dependent prostate cancer Cell CW22Rv1 with a concomitant reduction in PSA levels in an athymic nude mice xenograft model As shown in FIG. 9, normal prostate epithelial cells did not exhibit any significant cell death when treated with Lupeol up to a concentration of 50 μM for 48 hours. At 60 μM of Lupeol treatment for 48 hours, normal prostate epithelial cells exhibited 30% cell death.

As shown in FIG. 10 prostate cancer progresses from androgen dependent stage to highly metastatic androgen-independent stage. Androgen dependent prostatic cancer cells (LNCaP) exhibited highly significant (70%) cell death when treated with Lupeol up to a concentration of 30 µM for 48 hours. From 40-60 µM of Lupeol treatment for 48 hours, LNCaP cells exhibited 75-90% cell death.

Lupeol caused death of LNCaP cells by inducing apoptosis as is evident by flow cytometry data as shown in FIG. 11. Apoptosis is programmed cell death meant to eliminate unwanted cells and normal prostate cell have apoptotic machinery intact while as in prostate cancer cells this mechanism is disturbed.

Lupeol activates apoptotic machinery of LNCaP cells. The cleavage of PARP and Acinus protein is considered relevant biomarker for apoptosis. As shown in FIG. 12, Lupeol treatment for 48 hours induced cleavage of PARP and Acinus protein in prostate cancer cells.

Caspase proteins induce apoptosis (programmed cell death) of cells. In prostate cancer cells these caspases are in inactive form. Lupeol treatment to LNCaP cells induces the activation of Caspase-8 and 9 proteins which ultimately provide signal to cancer cells to undergo apoptosis.

As shown in FIG. 13, the treatment of Lupeol causes disappearance of inactive caspases which is a clear indication that caspases have been turned into active form which participate in the process of apoptosis.

Fas (also known as CD-95) is a death receptor protein and FADD is an adaptor protein which receives the death signal from FAS and transmits it to other proteins participating in apoptosis mechanism. Fas has a death domain sequence. Lupeol treatment induces the expression of FAS receptor protein and FADD protein in prostate cancer cells, as shown in FIG. 14. No other death receptor such as TNFR1, DR4/5 were activated by Lupeol (data not shown).

Anti-Fas antibody (anti-Fas mAb) activates the Fas protein. As shown in FIG. 15 LNCaP cells when treated with anti-Fas antibody, caused a 45% cell death in at a 1 µg at 48 hours of treatment. However when anti-Fas mAb pretreated LNCaP cells were treated with Lupeol (30 µg), there was 95-98% cell death. This result suggest that Lupeol acted in a significant synergistic manner and caused more cell death than the cumulative effects of Lupeol alone or ant-Fas antibody alone.

As seen in FIG. 16, Fas protein expression was found to be highly increased in anti-Fas mAb pretreated LNCaP cells treated with Lupeol. This result suggest that Lupeol has A potential to induce the Fas protein expression that ultimately leads to apoptotic cell death of prostate cancer cells.

To determine whether Lupeol induces apoptosis of LNCaP cells selectively through Fas receptor, we used siRNA technology. siRNA's have the ability to silence the of any specific protein. We designed siRNA against Fas receptor protein and treated LNCaP cell with them. The Fas protein expression was significantly reduced in LNCaP cells treated siRNA which suggested that these cells had no or minimal Fas receptor expression. When Fas-silenced LNCaP cells were treated with Lupeol, there was reduced cell death as compared to LNCaP cells (which had Fas receptors expression) treated with Lupeol. This data shown in FIG. 17 clearly suggests that Lupeol induced death of LNCaP cells is through Fas receptor.

To determine, whether lupeol could reduce the tumorigenicity of prostate cancer cells in animal model, androgen-dependent prostate cancer cells CW22Rv1, were implanted in a Athymic nude mouse xenograft model. Mice were given i.p. injection of Lupeol (1 mg/animal) three times a week. Tumor growth was measured weekly in terms of volume of tumors as function of time. The tumor growth in Lupeol treated mice was significantly Lower than control mice, as shown in FIG. 18.

CW22Rv1 cells once implanted in a xenograft mouse model releases Prostate specific antigen (PSA) in host system and grows rapidly than LNCaP cells. PSA is a well known diagnostic biomarker of prostate cancer. Mice treated with Lupeol exhibited lower serum PSA levels as compared with control mice, as shown in FIG. 19.

III. Lupeol and Pancreatic Cancer

Lupeol, a multi-target triterpene, induces apoptotic cell death of pancreatic cancer cells (ASPC1) through modulation of PI3K/Akt and NFkB signaling pathways: involvement of Ras/Protein kinase C/Ornithine Decarboxylase proteins.

Pancreatic cancer cells (ASPC-1) exhibited highly significant dose dependent cell death when treated with Lupeol for 24-72 hours, as shown in FIG. 20.

Lupeol caused death of ASPC-1 cells by inducing apoptosis as is evident by flow cytometry and confocal microscopy, as shown in FIG. 21. Apoptosis is programmed cell death meant to eliminate unwanted cells and normal pancreatic cells have apoptotic machinery intact while as in pancreatic cancer cells this mechanism is disturbed.

Lupeol activates apoptotic machinery of ASPC-1 cells. The cleavage of PARP and induction of pro-apoptotic Bax protein is considered relevant biomarker for apoptosis. Lupeol treatment for 48 hours induced cleavage of PARP and increased Bax protein expression in ASPC-1 cells. However no change was observed in the expression level of anti-apoptotic protein Bcl-2, as shown in FIG. 22.

Ras is an oncogenic protein and its levels have been reported to be increased in pancreatic cancer patients. Lupeol treatment to ASPC-1 cells caused a decrease in the expression of Ras protein. Ras activates PKCα protein which in turn regulates ornithine decarboxylase (ODC). ODC is a well known protein involved in the promotion of various types of cancers. Ras is also reported to regulate PI3 KB/Akt signaling pathways in pancreatic cancer. Lupeol caused a significant reduction in the protein expression of PKCa and ODC in ASPC-1 cells. Lupeol treatment also caused reduction in the phosphorylation of Akt which is a critical event in pancreatic cancer development, as shown in FIG. 23.

PI3KB/Akt signaling is reported to activate the anti-apoptotic and tumor cell survival pathways such as nuclear factor kappa B (NFkB) pathway in various types of cancer. NFkB activation is mediated through the phosphorylation of IkBα. This is followed by phosphorylation of NFkB that allows it to translocate to nucleus and activate tumor cell survival mechanism.

Lupeol caused a significant reduction in the phosphorylation of IkBα in ASPC-1 cells. Lupeol treatment also caused reduction in the phosphorylation of NFkB ASPC-1 cells which is a critical event in cancer development, as shown in FIG. 24.

MAP kinase signaling (p38, Erk1/2) is reported to activate the tumor cell survival pathways in various types of cancers. Lupeol caused a significant reduction in the phosphorylation of p38 in ASPC-1 cells. Lupeol treatment also caused an increase in the phosphorylation of Erk 1/2 cells. Erk 1/2 has been reported to play role both in apoptosis and tumor cell survival. In ASPC-1 cells Erk 1/2 expression was low and lupeol treatment was observed to induce its expression concomitant with increased cell death. P 21 is a known cell cycle inhibitor and Cyclin D-2 is reported to be increased during cancer development. These are important cell cycle regulators. Lupeol was observed to cause an increase in the expression of p-21 with a concomitant decrease in Cyclin-D2 protein expression, as shown in FIG. 25.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

REFERENCES (1) Afaq F, Adhami V M, Ahmad N and Mukhtar H. (2003). *Oncogene.*, 22, 1035-1044.
(2) Ahmad N, Gilliam A C, Katiyar S K, O'Brien T G and Mukhtar H. (2001). *Am. J. Pathol.*, 159, 885-892.
(3) Ahmad N, Gupta S, Husain M M, Heiskanen K M and Mukhtar H. (2000). *Clin. Cancer Res.*, 6, 1524-1528.
(4) Anjaneyulu V, Prasad K H and Rao G S. (1982). *Indian J. Pharm. Sci.*, 44, 58-59.
(5) Auvinen, M. (1997). *J. Natl. Cancer Inst.*, 89, 533-537.
(6) Badria F A, Mikhaeil B R, Maatooq G T and Amer M M. (2003). *Z. Naturforschfa[C].*, 58, 505-516.
(7) Baeuerle P A and Baltimore D. (1996). *Cell*, 87, 13-20.
(8) Baldwin A S. Jr. (1996). *Annu. Rev. Immunol.*, 14, 649-683.
(9) Beveridge T H, Li T S and Drover J C. (2002). *J. Agric. Food Chem.*, 50, 744-750.
(10) Bhimani R S, Troll W, Grunberger D and Frenkel K. (1993). Inhibition of oxidative stress in HeLa cells by chemopreventive agents. *Cancer Res.*, 53, 4528-4533.
(11) Bickers D R and Athar M. (2000). *J. Dermatol.*, 27, 691-695.
(12) Bours V, Bentires-Alj M, Hellin A C, Viatour P, Robe P, Delhalie S, Benoit V, and Merville M P. (2000). *Biochem. Pharmacol.*, 60, 1085-1089.
(13) Callejas N A, Casado M, Bosca L and Martin-Sanz P. (1999). *J. Cell. Sci.*, 18, 3147-3155.
(14) Carpenter C L and Cantley L C. (1996). *Curr. Opin. Cell. Biol.*, 8, 153-158.
(15) Chun K S, Kang J Y, Kim O H, Kang H and Surh Y J. (2002). *J. Environ. Pathol. Toxicol. Oncol.*, 21, 131-139.
(16) Conney A H, Lou Y R, Xie J G, Osawa T, Newmark H L, Liu Y, Chang R L and Huang M T. (1997) *Proc. Soc. Exp. Biol. Med.*, 216, 234-245.
(17) DiGiovanni J. (1991). Modification of Tumor Development in Rodents: Progress in Experimental Tumor Research. Ito N and Sugano H (ed). Karger: Basel, 33, pp. 192-229.
(18) DiGiovanni J. (1992). *Pharmacol. Ther.*, 54, 63-128.
(19) Dos Santos Pereira A and De Aquino Neto F R. (2003). *Z Naturforsch [C]*, 58, 201-206.
(20) Downward J. (1998). *Curr. Opin. Cell Biol.*, 10, 262-267.
(21) Einspahr J G, Bowden G T, and Alberts D S. (2003). *Recent Results Cancer Res*, 163, 151-164.
(22) Epinat J C and Gilmore T D. (1999). *Oncogene.*, 18, 6896-6909.
(23) Fernandez M A, de las Heras B, Garcia M D, Saenz M T and Villar A. (2001). *J. Pharm. Pharmacol.*, 53, 1533-1539.
(24) Fournet A, Angelo A, Munoz V, Roblot F, Hocquemiller R and Cave A. (1992). *J. Ethnopharmacol.*, 37, 159-164.
(25) Furstenberger G and Marks F. (1985). *Arachidonic Acid Metabolism and Tumor Promotion.* Fischer S M and Slaga Ti (ed). Martinus Nijhoff Publishing: Boston, pp. 49-72.
(26) Geetha T and Varalakshmi P. (1999). *Mol. Cell Biochem.*, 201, 83-87.
(27) Geetha T and Varalakshmi P. (2001). *J. Ethnopharmacol.*, 76, 77-80.
(28) Guevara A P, Amor E and Russell G. (1996). *Mutat. Res.*, 361, 67-72.
(29) Gupta S, Ahmad N, Mohan R R, Husain M M and Mukhtar H. (1999). *Cancer Res.*, 59, 2115-2120.
(30) Gupta 5 and Mukhtar H. (2001). *Skin Pharmacol. Appl. Skin Physiol*, 14, 373-385.
(31) Gupta S and Mukhtar H. (2002). *Cancer Metastasis Rev.*, 21, 363-380.
(32) Hasmeda M, Kweifio-Okai G, Macrides T and Polya G M. (1999). *Planta Med.*, 65, 14-18.
(33) Hata K, Hori K and Takahashi 5. (2002). *J. Nat. Prod.*, 65, 645-648.
(34) Hata K, Hori K and Takahashi S. (2003). *J. Biochem* (Tokyo), 134, 441-445.
(35) Herschman H. R. (1994). *Cancer Metastasis Rev.*, 13, 241-256.
(36) Hodges L D, Kweifio-Okai G and Macrides T A. (2003). *Mol. Cell. Biochem.*, 252, 97-101.
(37) Israel A. (1995). *Trends Genet.*, 11, 203-205.
(38) Kakuda R, Iijima T, Yaoita Y, Machida K and Kikuchi M. (2002). *Phytochemistry.*, 59, 791-794.
(39) Katiyar S K, Agarwal R and Mukhtar H. (1996). *Cancer Res.*, 56, 1023-1030.
(40) Katiyar S K and Mukhtar H. (1997). *Carcinogenesis.*, 18, 1911-1916.
(41) Katiyar S K Challa A, McCormick T S, Cooper K D and Mukhtar H. (1999). *Carcinogenesis.*, 20, 2117-2124.
(42) Katiyar S K, Mohan R R, Agarwal R and Mukhtar H. (1997). *Carcinogenesis.*, 18, 497-502.
(43) Kim D J, Shin D H, Ahn B, Kang J S, Nam K T, Park C B, Kim C K, Hong J T, Kim Y B, Yun Y W, Jang D D and Yang K H. (2003). *Mutat Res.*, 523-524, 99-107.
(44) Liang Y C, Tsai D C, Lin-Shiau S Y, Chen C F, Ho C T and Lin J K. (2002). *Nutr. Cancer,* 42, 217-223.
(45) Lin L C, Chou C J and Kuo Y C. (2001). *J. Nat. Prod.*, 64, 674-676.
(46) Luo J, Manning B D and Cantley L C. (2003). *Cancer Cell.*, 4, 257-262.
(47) Maniatis T. (1997). *Science.*, 278, 818-819.
(48) Mills G B, Kohn E, Lu Y, Eder A, Fang X, Wang H, Bast R C, Gray J, Jaffe R and Hortobagyi G. (2003). *Semin. Oncol.*, 30, 93-104.
(49) Miura K, Kikuzaki H and Nakatani N. (2001). *Phytochemistry.*, 58, 1171-1175.
(50) Mohan R R, Challa A, Gupta S, Bostwick D G, Ahmad N, Agarwal R, Marengo S R, Amini S B, Paras F, MacLennan G T, Resnick M I and Mukhtar H. (1999). *Clin. Cancer Res.*, 5, 143-147.
(51) Moriarity D M, Huang J, Yancey C A, Zhang P, Setzer W N, Lawton R O, Bates R B and Caldera S. (1998). *Planta Med.*, 64, 370-372.
(52) Nagaraj M, Sunitha 5 and Varalakshmi P. (2000). *J. Appl. Toxicol.*, 20, 413-417.
(53) Nakadate T, Aizu E, Yamamoto S, Fujiki H, Sugimura T and Kato R. (1985). *Jpn. J. Pharmacol.*, 37, 253-258.
(54) Nikiema J B, Vanhaelen-Fastre R, Vanhaelen M, Fontaine J, De Graef C and Heenen M. (2001). *Phytother. Res.*, 15, 131-134.
(55) Osaki M, Kase S, Adachi K, Takeda A, Hashimoto K and Ito H. (2004) *J. Cancer Res. Clin. Oncol.*, 130, 8-14.
(56) Rajic A, Kweifio-Okai G, Macrides T, Sandeman R M, Chandler D S and Polya G M. (2000). *Planta Med.*, 66, 206-210.
(57) Romashkova J A and Makarov S S. (1999). *Nature.*, 401, 86-90.
(58) Saeed M A and Sabir A W. (2002). *Fitoterapia.*, 73, 417-420.

(59) Saleem M, Alam A, Arifin S, Shah M S, Ahmed B and Sultana S. (2001). *Pharmacol. Res.*, 43, 127-134.
(60) Saleem R, Ahmad S I, Ahmed M, Faizi Z, Zikr—the inventors'—Rehman S, Ali M and Faizi S. (2003). *Biol. Pharm. Bull.*, 26, 41-46.
(61) Seo H J, Park K K, Han S S, Chung W Y, Son M W, Kim W B and Surh Y J. (2002). *Int. J. Cancer.*, 100, 456-462.
(62) Smith W L, Garavito R M and DeWitt D L. (1996). *J. Biol. Chem.*, 271, 33157-33160.
(63) Sosa A. (1963). *Bull. Soc. Chim. Bio.* (Paris)., 45, 117-126.
(64) Stambolic V, Mak T W and Woodgett J R. (1999). *Oncogene.*, 18, 6094-6103.
(65) Sunitha S, Nagaraj M and Varalakshmi P. (2001). *Fitoterapia.*, 72, 516-523.
(66) Surh Y J. (2003). *Nat. Rev. Cancer.*, 3, 768-780.
(67) Thomas T and Thomas T J. (2003). J. Cell. Mol. 113-126.
(68) Ulubelen A, Topcu G and Johansson C B. (1997). *J. Nat. Prod*, 60, 1275-1280.
(69) Verma A K, Shapas B G, Rice H M and Boutwell R K. (1979). *Cancer Res.*, 39, 419-425.
(70) Vidya L, Lenin M and Varalakshmi P. (2002). *Phytother. Res.*, 16, 514-518.
(71) Wada S, Iida A and Tanaka R. (2001). *J. Nat. Prod.*, 64, 1545-1547.
(72) Ziegler H L, Staerk D, Christensen J, Hviid L, Hagerstrand H and Jaroszewski J W. (2002). *Antimicrob. Agents Chemother.*, 46, 1441-1446.

What is claimed is:

1. A method of treating prostate cancer comprising parenterally administering to a human in need thereof a therapeutically effective amount of a parenteral composition comprising an anticancer compound having the formula:

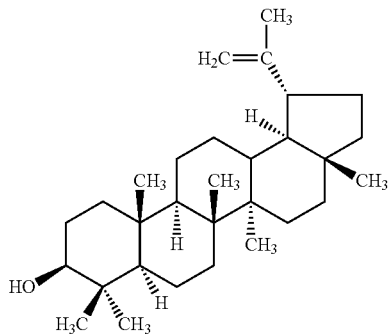

or a pharmaceutically acceptable salt thereof, and,
a parenteral vehicle,
wherein the compound treats prostate cancer in a dose dependent manner.

2. A method according to claim 1, wherein the parenteral vehicle is a member selected from the group consisting of sodium chloride solution, Ringer's dextrose, dextrose and sodium chloride, lactated Ringer's and fixed oils.

3. A method according to claim 2, wherein the parenteral vehicle is an intravenous vehicle.

4. A method according to claim 3, wherein the intravenous vehicle is a member selected from the group consisting of fluid replenisher, nutrient replenisher, and electrolyte replenisher.

5. A method according to claim 3, wherein the parenteral composition further comprises one or more members selected from the group consisting of an antimicrobial, antioxidant, collating agent, and inert gas.

* * * * *